(12) United States Patent
Lipkowski et al.

(10) Patent No.: US 6,875,759 B1
(45) Date of Patent: Apr. 5, 2005

(54) SUBSTITUTED GUANIDINES AND THE USE THEREOF

(75) Inventors: Andrzej W. Lipkowski, Warsaw (PL); Kelvin Gee, Irvine, CA (US)

(73) Assignee: Kadmus Pharmaceuticals, Irvine, CA (US)

( * ) Notice: Subject to any disclaimer, the term of this patent is extended or adjusted under 35 U.S.C. 154(b) by 209 days.

(21) Appl. No.: 09/625,196

(22) Filed: Jul. 21, 2000

Related U.S. Application Data

(60) Provisional application No. 60/144,810, filed on Jul. 21, 1999.

(51) Int. Cl.⁷ .................. A61K 31/33; A61K 31/495; C07D 241/00; C07D 295/00
(52) U.S. Cl. .................. 514/183; 514/252.12; 514/634; 544/358; 544/401; 544/403
(58) Field of Search .................. 514/183, 252.12; 544/634, 358, 402, 403

(56) References Cited

U.S. PATENT DOCUMENTS

| | | | |
|---|---|---|---|
| 3,501,557 A | 3/1970 | Brois et al. | 260/978 |
| 3,961,056 A | 6/1976 | DuCharme | 424/248 |
| 4,281,004 A | 7/1981 | Ives | 424/263 |
| 4,686,283 A | 8/1987 | Nestor et al. | 530/327 |
| 4,709,094 A | 11/1987 | Weber et al. | 564/238 |
| 4,906,779 A | 3/1990 | Weber et al. | 564/238 |
| 5,093,525 A | 3/1992 | Weber et al. | 564/238 |
| 5,190,976 A | 3/1993 | Weber et al. | 514/634 |
| 5,262,568 A | 11/1993 | Weber et al. | 564/238 |
| 5,312,840 A | 5/1994 | Keana et al. | 514/634 |
| 5,385,946 A | 1/1995 | Keana et al. | 514/634 |
| 5,403,861 A | 4/1995 | Goldin et al. | 514/634 |
| 5,478,863 A | 12/1995 | Keana et al. | 514/634 |
| 5,502,255 A | 3/1996 | Keana et al. | 564/230 |
| 5,510,380 A | 4/1996 | Seoane et al. | 514/613 |
| 5,574,070 A | 11/1996 | Keana et al. | 514/634 |
| 5,604,228 A | 2/1997 | Keana et al. | 514/255 |
| 5,608,106 A | 3/1997 | Fried et al. | 562/538 |
| 5,614,630 A | 3/1997 | Goldin et al. | 546/159 |
| 6,057,371 A | 5/2000 | Glennon | 514/649 |
| 6,103,719 A | 8/2000 | Esser et al. | 514/235.8 |

FOREIGN PATENT DOCUMENTS

| | | |
|---|---|---|
| DE | GB0618147 | 8/1906 |
| DE | 355121 | 6/1922 |
| DE | 19824470 A1 | 12/1999 |
| EP | 86300123.6 | 7/1986 |
| EP | 0 188 333 B1 | 7/1989 |
| JP | 57-24366 | 2/1982 |
| JP | 55099171 | 2/1982 |
| WO | WO 90/14067 | 11/1990 |
| WO | WO 91/09594 | 7/1991 |
| WO | WO 91/12797 | 9/1991 |
| WO | WO 91/13056 | 9/1991 |
| WO | WO 91/18868 | 12/1991 |
| WO | WO 92/14697 | 9/1992 |
| WO | WO 93/00313 | 1/1993 |
| WO | WO 88/00583 | 1/1998 |
| WO | WO 98/23267 | 6/1998 |
| WO | WO 99/62893 | 12/1999 |
| WO | WO 00/72800 | 12/2000 |
| WO | WO 00/72840 | 12/2000 |

OTHER PUBLICATIONS

Thomas et al, J. Medicinal Chem. 32/1,228–36(1989), also cited as Chemical Abstract DN:110:38957.*
Sartippour et al, PubMed Abstract 12680218, also cited as Anticancer Res. 23/1,231–4 (2003).*
Burd et al(PubMed Abstract 12600235, also cited as Radiat. Res. 159/3,328–35(2003).*
Uckun et al(Current Cancer Drug Targets, 1,59–71 (2001).*
Celi Textbook of Medicine, Edited by Bennett et al, W.B.Saunders Co.,1996, pp. 1004–1010.*
PubMed Abstract 12677247, also cited as Drug News Perspect 15/10,626–6322002).*
PubMed Abstract 12760986 also cited as Anesth. Analg. 96/6, 1631–5(2003).*
PubMed Abstracxt 10856067, also cited as BMJ 320/7250, 1642–6(2000).*
Thomas E.W. et al,"J. of Med. Chemistry",Synthesis of acylguanidine analogs; 32/1, 228–36(1989).*
Adler, P., et al., "The effect of structurally different local anesthetics on the cholinesterase activity of human serum," Zeitschrift fuer Vitamin, Hormon, und Fermentforschung (1950) 3, 236–43 Abstract (German).
Bender, "The formation of guianidine derivs . . . " Ann. Univ. Sci. Budapest Rolando Eotvos Nominaiae Sect. Chim 1, 136–41 (1959) Abstract German.

(Continued)

Primary Examiner—Richard L. Raymond
Assistant Examiner—Sudhaker B. Patel
(74) Attorney, Agent, or Firm—Orrick, Herrington & Sutcliffe

(57) ABSTRACT

A method for the treatment of cancer and pain in an animal subject is disclosed, comprising administering to said animal in need of such treatment an effective amount of a compound of formula I:

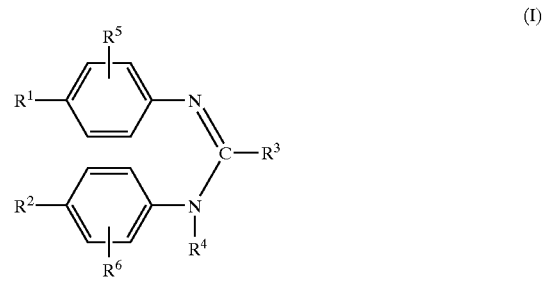

wherein $R^1$–$R^6$ are defined herein. Pharmaceutical compositions comprising one or more compounds of formula I and a pharmaceutically acceptable carrier are also disclosed.

6 Claims, 8 Drawing Sheets

OTHER PUBLICATIONS

Doughty, M.B., et al., "Non–peptide Mimics of Neuropeptide Y: Analysis of Benextramine Structure–Activity Relationships at $Y_1$ and $Y_2$ Receptors," Peptides: Chemistry, Structure and Biology 1996.

Humphrey, S.J., et al., "Cardiovascular Effects of the K–ATP Channel Blocker U–37883A and Structurally Related Morpholinoguanidines," Meth. Find. Exp. Clin Pharmacol. 1996 18(4): 247–260.

Kishore, Vimal et al., "Anti–Inflammatory and Antiproteolytic Properties of Substituted Guanidines," Pharmacology 15: 97–103 (1977).

Knieps, S., et al., "ω–Phenyl–ω–(2–pyridyl)alkyl–substituted bisguanidines are moderate neuropeptide Y antagonists," Pharm Pharmacol. Let 6 (1996) 1: 27–10.

LeBrocq, C.N., "Local Anesthetics Recommended as Substitutes for Cocaine,": Pharmaceutical Journal (1909) 82, 673–674.

Siddiqui, N., et al., "Analgesic and hypnosis potentiation effect of some 1–(2–benzothiazolyl)1–aryl–3–phenyl–4–aryl guanidines," Indian Journal of Experimental Biology, vol. 30, Sep. 1992, pp. 811–813.

Adock, B. and Lawson, A., "2–Amino–2–imidazolines and 2–Amino–2–oxazolines. Part II.," Journal of The Chemical Society 474–479, The Chemical Society, Burlington House (1965).

Dollinger, H. et al., "New guanidine and amidine derivatives useful in treatment of e.g. inflammatory and allergic conditions, central nervous system disorders, tumors, herpes zoster, etc.," Dialog File 351, WPI Acc. No. 2000–063491/200006, Derwent WPI English language abstract of DE 19824470 (Document AM3).

Doughty, M.B. et al., "Non–peptide Mimics of Neuropeptide Y: Analysis of Benextramine Structure–Activity Relationships at $Y_1$ and $Y_2$ Receptors," in Peptides: Chemistry, Structure and Biology, Kaumaya, P.T.P. and Hodges, R.S., eds., Mayflower Scientific Ltd., England, pp. 711–712 (1996).

Dyson, G.M. and Harrington, T., "The Action of Chlorine on Aryl Thiocarbimides and the Reactions of Aryl isoCyanodichlorides," Journal of The Chemical Society 191–194, The Chemical Society, Burlington House (1940).

Fridland, S.V. et al., "Reaction of N,N'–Diphenylguanidine with Esters of Methylphosphonic Acid," Zhurnal Obshchei Khimii 66:791–793, Maik Nauka/Interperiodica Publishing (1996).

Fridland, S.V. et al., "Reaction of N,N'–Diphenylguanidine with Esters of Methylphosphonic Acid," Russian Journal of General Chemistry 66:772–773, Maik Nauka/Interperiodica Publishing (1996).

Humphrey, S.J. et al., "Cardiovascular Effects of the K–ATP Channel Blocker U–37883A and Structurally Related Morpholinoguanidines," Methods and Findings in Experimental and Clinical Pharmacology 18:247–260, Prous Science (1996).

Jefferson, R. et al., "Chloroboration and Allied Reactions of Unsaturated Compounds. Part IV. Boration of Di–p–Tolyl–carbodi–imide," Journal of The Chemical Society (A) 1584–1590, The Chemical Society, Burlington House (1966).

Kishore, V. et al., "Anti–Inflammatory and Antiproteolytic Properties of Substituted Guanidines," Pharmacology 15:97–103, S. Karger (1977).

Knieps, S. et al., "ω–Phenyl–ω–(2–pyridyl)alkyl–substituted bisguanidines are moderate neuropeptide Y antagonists," Pharmaeutical and Pharmacological Letters 6:27–30, medpharm Scientific Publishers (1996).

Ram, V.J. et al., "Synthesis of Some New Thioureas and Guanidines Derived from p–Amino n–Butyl and Iso–Butyl Benzoates," The Indian Journal of Pharmacy 35:30–32, The Indian Pharmaceutical Association (1973).

Ramadas, K. et al., "A Short and Concise Synthesis of Guanidines," Synlett 9:1053–1054, Thieme Stuttgart (1997).

Shionogi & Co Ltd., "Carcinostatic 2–(1–imidazolyl) amidine cpds.—preptd. from phenyl–thiourea deriv. and N,N'–thionyl–diimidazole," Dialog File 351, WPI Acc No. 1982–21122E/198211, Derwent WPI English language abstract of JP 57–24366 (Document AL1).

Siddiqui, N. et al., "Synthesis of Benzothiazolyl Guanidine Derivatives as Potent Anticonvulsants," Pharmakeftiki 5:121–125, Pharmaceutical Publications Ltd. (1992).

Siddiqui, N. and Pandeya, S.N., "Analgesic and hypnosis potentiation effect of some 1–(2–benzothiazolyl)–1–aryl–3–phenyl–4–aryl guanidines," Indian J. of Exp. Biol. 30:811–813, Publications & Information Directorate (1992).

Singh, T. et al., "E.P. Activity Assessment of Certain Nitrogen and Sulphur Heterocyclic Compounds as Potential Additives in Four Ball Test©," Lubrication Engineering 46:681–685, The Society of Tribologists and Lubrication Engineers (1990).

Szekerke, M. and Csazar, J., "Reaction readiness of carbodiimides with primary amines," Chemical Abstracts 56:col. 4591, line 82, through col. 4592, line 13, The American Chemical Society (1962).

Thomas, E.W. et al., "Synthesis of Acylguanidine Analogues: Inhibitors of ADP–Induced Platelet Aggregation," Journal of Medicinal Chemistry 32:228–236, American Chemical Society (1989).

Zhelyazkov, L. and Baeva, V., "Synthesis of substituted thiocarbamides and derivatives containing guanidine groups," Tr. Nauchnoizsled. Khim–Farm. Inst 7:69–78, Tekhnika (1972).

Zhelyazkov, L. and Baeva, V., "Synthesis of substituted thiocarbamides and derivatives containing guanidine groups," Chemical Abstracts 79:422, abstract 31640u, The American Chemical Society (1973).

International Search Report for International Application No. PCT/US00/19938, mailed Feb. 6, 2001.

* cited by examiner

SUBSTITUTED GUANIDINES AND THE USE THEREOF

CROSS REFERENCE TO RELATED APPLICATION

This application claims the benefit of U.S. Provisional application 60/144,810, filed Jul. 21, 1999, the contents of which are fully incorporated by reference herein.

BACKGROUND OF THE INVENTION

1. Field of the Invention

The invention is in the fields of organic and medicinal chemistry. In particular, the invention relates to substituted diarylguanidines and analogs and derivatives thereof which are useful for the treatment or prevention of cancer and pain.

2. Related Art

Estimates from the World Health Organization indicated that there are approximately 8.1 million new cases of cancer and 5.2 million cancer deaths each year. In 1998 the American Cancer Society estimates that 1.2 million Americans were diagnosed with cancer and 565,000 people died of the disease and approximately 8 million people are living with a diagnosis of cancer. Even though important strides have been made in cancer detection a number of new agents have been introduced into clinical use the overall 5-year survival for patients with cancer is still only 40% and long-tern survival in the rest of the world is even worse. Most experts agree that little progress has been made in improving the outcome of a cancer patient and achieving a cure continues to be an elusive goal. Cancer is a heterogeneous collection of diseases. Consequently, various treatment strategies do not exhibit equal efficacy in all cancers. When the tumor is small and localized, surgery alone may be sufficient to produce a cure. However, in patients where the tumor may have spread, surgery may provide only limited benefits. In such cases chemotherapy and/or radiation therapy may be used to treat advanced or metastatic disease. However, it is rare that such treatments will produce a cure.

Chemotherapy generally involves the administration of one or more, often, cytotoxic agents. Unlike surgery and radiation that are used for the treatment of local and regional disease, these drugs are distributed systemically and will usually exhibit some degree of efficacy in local, regional, and metastatic disease. Early drugs tended to damage DNA and derived some measure of selectivity by targeting rapidly proliferating populations of cells. Recent advances in cell and molecular biology have allowed pharmaceutical scientists to develop a number of new mechanism-based agents (e.g. taxol, gemcitabine, topotecan, etc.). These drugs potentially offer greater selectivity and reduced toxicity as they attempt to target biochemical or molecular pathways that are inherent to the malignant phenotype. However, most of these drugs are extremely toxic and in many cases the amount of drug that can be delivered is limited by potentially life threatening systemic toxicity. As a result these drugs must often be administered at suboptimal doses thereby limiting their efficacy. In addition, while many cancers will initially respond to one or more drugs, tumor cells often become resistant to a broad spectrum of chemotherapeutic agents leading to disease progression and ultimately death.

Traditionally, cancer has been thought of as a disease of abnormal cell proliferation. This belief has provided the basis for die development of most of the currently used chemotherapeutic agents. Although these drugs are extremely cytotoxic, it was hoped that selectivity could be achieved as a result of the drugs being taken up, to a greater extent, by the rapidly proliferating cancer cells. While this approach has lead to a number of important and clinically active compounds, dose-limiting toxicity continues to be a major problem.

Only recently have we begun to understand that increased cell proliferation is not the only cause of tumor progression and that tumors can develop as a result of decreased cell death. Programmed cell death or apoptosis is a normal process through which damaged or senescent cells are eliminated. Apoptosis is an active and genetically programmed process that is highly regulated requiring gene transcription and the synthesis of specific proteins (Staunton, M. J. and Gaffney, E. F., *Arch. Pathol. Lab. Med.* 122:310 (1998); Hetts, S. W., *J.A.M.A.* 279:300 (1998)). Regulation of apoptosis occurs at three levels and involves cell survival or death signals, cell survival or death regulators, and cell death effector.

Exposure to growth promoting factors, such as neuropeptides, causes the cell to progress through the cell cycle. In cases where a cell's DNA becomes damaged, cell cycle arrest occurs until such time that the DNA can be repaired. If the damage cannot be repaired or if the survival factors are withdrawn, the cell receives a signal to undergo apoptosis (Hetts, S. W.,*J.A.M.A.* 279:300 (1998)). However, whether or not a cell undergoes apoptosis is controlled by cell death regulators or through the activation or inactivation of enzymes that function to break down the cells prior to their removal by phagocytosis.

Apoptotic cells exhibit membrane blebbing, nucleus condensation, DNA fragmentation, and changes in mitochondria membrane permeability. At the biochemical and molecular level, caspase, a protease, is activated as a consequence of leakage of Cytochrome C from the mitochondria, and there is an increase in the expression of a number of apoptotic genes, including p53, bax, and gadd.

A variety of neuropeptide receptors have been detected in human cancer cells and in many cases the tumor cells not only respond to but also synthesize and release neuropeptides as part of an autocrine loop (Cuttitta, F., et al., *Nature* 316:823 (1985)). Moreover, neuropeptides are increasingly implicated in control of cancer cell proliferation (Moody, T. W., et al., *Life Sci.* 37:105 (1985); Mahmoud, S., et al., *Cancer Res.* 51:1798 (1991)). Peptides of the substance P, bombesin, gastrin, and cholecystokinin family of peptides initiate a complex cascade of events that promotes cell survival and proliferation (Sethi, T. and Rozengurt, E., *Cancer Res.* 51:3621 (1991)). Within this context, antagonists with a broad spectrum of activity that interfere with the signal transduction pathways of this family of proteins would be of special interest as they would likely inhibit cell proliferation and induce apoptosis.

The activities of several peptide drugs that antagonize the actions of neuropeptides have previously been described. See, e.g., Hennig, I. M., et al., *Int. J. Cancer* 61:786 (1995); Layton, J. E., et al., *Cancer Res.* 48:4783 (1988); Bepler, G., et al., *Peptides* 9:1367 (1988); Bunn, P. A., Jr., et al., *Cancer Res.* 54:3602 (1994); Seckl, M. J., et al., *Cancer Res.* 57:51 (1997); Langdon, S., et al., *Cancer Res.* 52:4554 (1992); Woll, P. J. and Rozengurt, E., *Proc. Natl. Acad. Sci. U.S.A.* 85:1859 (1988); Woll, P. J. and Rozengurt, E., *Cancer Res.* 50:3968 (1990); Jarpe, M. B., et al.,*J. Biol. Chem.* 273:3097 (1998). These agents block neuropeptide-mediated signal transduction and initiate apoptosis in cancer cells while having no effect on normal cells where these peptides are not mitogenic (Jarpe, M. B. et al., *J. Biol. Chem.* 273:3097

(1998)). While active in vitro, these agents are rapidly degraded, and exhibit poor bioavailability when administered to animals. As a result, these agents tend to exhibit antitumor activity in vivo only when administered in close proximity to the tumor making their use in cancer chemotherapy impractical (Jones, D. A., et al., *Peptides* 18:1073 (1997); Jones, D. A., et al., *Gen. Pharmacol.* 28:183 (1997); Davis, T. P., et al., *Peptides* 13:401 (1992); Halmos, G. and Schally, A. V., *Proc. Natl. Acad. Sci. U.S.A.* 94:956 (1997)).

Some diarylguanidine derivatives have previously been described and used in a variety of applications, for example:

Dyson, G. M., and Harrington, T., *J. Chem. Soc.* 191–194 (1940) discloses the synthesis of N-phenyl-N',N''-di-p-tolyl-guanidine.

Adcock, B., and Lawson, A., *J. Chem Soc.* 474–479 (1965) discloses the synthesis of N-(2-chloroethyl)-N',N''-diphenylguanidine.

Jefferson, R., et al., *J. Chem. Soc. A*, 1584–1590 (1966) discloses the synthesis of some N-dialkyl-N',N''-di-p-tolyl-guanidine derivatives.

Ram, V. J., et al., *Indian J. Pharm.* 35:30–32 (1973) discloses the synthesis of some guanidines derived from p-amino, n-butyl and iso-butyl benzoates.

Thomas, E. W., et al., *J. Med. Chem.* 32:228–236 (1989) discloses the use of some heterocyclic N,N'-di-p-tolyl-guanidine compounds as inhibitors of ADP-induced platelet aggregation.

Singh, T., et al., *Lubrication Engineering* 46:681–685 (1990) discloses the use of some N-2-benzothiazolyl-N,N', N''-triarylguanidines as additives for lubricating oil.

Siddiqui, N., et al., *Pharmakeftiki* 5:120–124 (1992) discloses the synthesis of some N-2-benzothiozolyl-N,N', N''-triarylguanidine derivatives and the use of these compounds as anticonvulsants.

Fridland, S. V., et al., *Zh. Obschch. Khim.* 66:791–793 (1996) discloses the synthesis of some N-alkyl-N',N''-diphenylguanidines.

Ramadas, R., et al., *Synlett* 9:1053–1054 (1997) discloses the synthesis of some N-alkyl-N',N''-diphenylguanidines.

U.S. Pat. No. 3,501,557 discloses a process for preparing some 2-aminoethyl-thiophosphate salts.

U.S. Pat. No. 4,281,004 discloses the use of some phenylguanidine derivatives as hypoglycemic agents.

U.S. Pat. No. 4,686,283 discloses some polypeptide analogs of transforming and epidermal growth factor fragments for use as therapeutic and diagnostic agents.

U.S. Pat. No. 5,510,380 discloses some nonpeptide bradykinin antagonists.

U.S. Pat. No. 5,608,106 discloses some salts of pyromellitic acid and their use as epoxy resin curing agents.

European Patent Publication 188333 discloses some guanidine derivatives and their use as anti-inflammatory agents.

Described herein are a series of diarylguanidine compounds that selectively induce apoptosis in cancer. These compounds exhibit significant anticancer activity both in vitro and in vivo providing an alternative approach for treating cancer that may translate into an improvement in long-term survival.

SUMMARY OF THE INVENTION

A first aspect of the present invention is directed to a method for the treatment of cancer or pain in an animal subject, comprising administering to said animal in need of such treatment an effective amount of a compound of formula I:

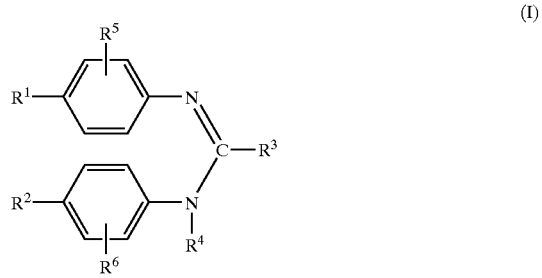

(I)

wherein, $R^1$ and $R^2$ are each independently selected from the group consisting of (a) hydrogen, halogen, hydroxy, cyano, amino, nitro, acylamido, thiol, azido, formyl, carboxy, carbonylamido and (b) aryl, fused aryl, carbocyclic, heterocyclic, heteroaryl, alkyl, alkenyl, alkyl, arylalkyl, arylalkenyl, arylalkynyl, heteroarylalkyl, heteroarylalkenyl, heteroarylalkynyl, carbocycloalkyl, heterocycloalkyl, acyloxy, alkoxy, alkylthiol, alkoxyalkyl and alkylthioalkyl, each of which is optionally substituted by one or more substituents independently selected from the group consisting of halogen, hydroxy, cyano, methoxy, amino, nitro, acylamido, thiol, azido, formyl, carboxy and carbonylamido;

$R^3$ is selected from the group consisting of:

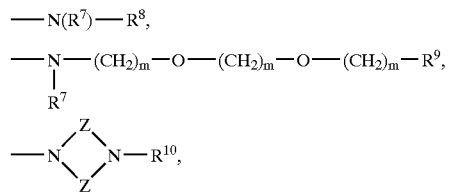

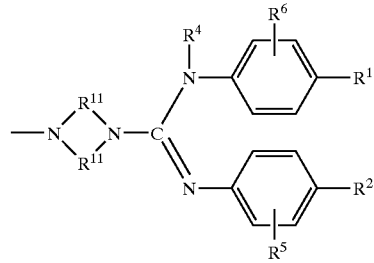

and a 2-amino sugar which is optionally substituted by one or more substituents independently selected from the group consisting of alkyl and alknoyl, and is substituted on the 2-amino nitrogen, where Z is a $(C_{1-6})$alkylene group, which is optionally substituted by one or more substitutents independently selected from the group consisting of (a) halogen, hydroxy, cyano, amino, nitro, acylamido, thiol, azido, formyl, carboxy, carbonylamido and (b) aryl fused aryl, carbocyclic, heterocyclic, heteroaryl, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, acyloxy, alkoxy, alkylthiol, alkoxyalkyl and alkylthioalkyl, each of which is optionally substituted by one or more substituents independently selected from the group consisting of halogen, hydroxy, cyano, methoxy, amino, nitro, acylamido, thiol, azido, formyl, carboxy and carbonylamido;

R⁴ is selected from the group consisting of (a) hydrogen and (b) aryl, fused aryl, carbocyclic, heterocyclic, heteroaryl, alkyl, alkenyl, alkynyl arylalkyl, arylalkenyl, arylalkynyl, heteroarylalkyl, heteroarylalkenyl, heteroarylalkynyl, carbocycloalkyl, heterocycloalkyl, alkoxyalkyl and alkylthioalkyl, COR, CO₂R and CONR$_x$R$_y$, each of which is optionally substituted by one or more substituents selected from the group consisting of halogen, hydroxy, cyano, methoxy, amino, nitro, acylamido, thiol, azido, formyl, carboxy and carbonylamido, wherein R, R$_x$ and R$_y$, are independently selected from the group consisting of hydrogen, aryl, fused aryl, carbocyclic, heterocyclic, heteroaryl, alkyl, alkenyl, alkynyl, alkoxyalkyl, alkylthioalkyl, arylalkyl, arylalkenyl, arylalkynyl, heteroarylalkyl, heteroarylalkenyl, heteroalkynyl, carbocycloalkyl and heterocycloalkyl; or R$_x$ and R$_y$ are taken together to form a heterocycle, which is optionally substituted by one or more substituents independently selected from the group consisting of halogen, hydroxy, cyano, methoxy, amino, nitro, acylamido, thiol, azido, formyl, carboxy and carbonylamido;

R⁵ and R⁶ are each zero to four substituents and are independently selected from the group consisting of (a) halogen, hydroxy, cyano, amino, nitro, acylamido, thiol, azido, formyl, carboxy, carbonylamido and (b) aryl, fused aryl, carbocyclic, heterocyclic, heteroaryl, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, acyloxy, alkoxy, alkylthiol, alkoxyalkyl and alkylthioalkyl, each of which is optionally substituted by one or more substituents independently selected from the group consisting of halogen, hydroxy, cyano, methoxy, amino, nitro, acylamido, thiol, azido, formyl, carboxy and carbonylamido;

R⁷ is selected from the group consisting of (a) hydrogen and (b) aryl, fused aryl, carbocyclic, heterocyclic, heteroaryl, alkyl, alkenyl, alkynyl, alkoxyalkyl, alkylthioalkyl, arylalkyl, arylalkenyl, arylalkynyl, heteroarylalkyl, heteroarylalkenyl, heteroarylalkynyl, carbocycloalkyl, heterocycloalkyl, COR, CO₂R and CONR$_x$R$_y$, each of which is optionally substituted by one or more substituents independently selected from the group consisting of halogen, hydroxy, cyano, methoxy, amino, nitro, acylamido, thiol, azido, formyl, carboxy and carbonylamido, wherein R, R$_x$ and R$_y$, are independently selected from the group consisting of hydrogen, aryl, fused aryl, carbocyclic, heterocyclic, heteroaryl, alkyl, alkenyl, alkynyl, alkoxyalkyl, alkylthioalkyl, arylalkyl, arylalkenyl, arylalkynyl, heteroarylalkyl, heteroarylalkenyl, heteroalkynyl, carbocycloalkyl and heterocycloalkyl; or R$_x$ and R$_y$ are taken together to form a heterocycle, which is optionally substituted by one or more substituents independently selected from the group consisting of halogen, hydroxy, cyano, methoxy, amino, nitro, acylamido, thiol, azido, formyl, carboxy and carbonylamido;

R⁸ is selected from the group consisting of aryl, fused aryl, carbocyclic, heterocyclic, heteroaryl, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, aminoalkyl, acyloxy, alkoxy, alkylthiol, alkoxyalkyl and alkylthioalkyl, each of which is optionally substituted by one or more substituents independently selected from the group consisting of (a) halogen, hydroxy, cyano, methoxy, amino, nitro, acylamido, thiol, azido, formyl, carboxy, carbonylamido and (b) alkoxycarbonyl, aryloxycarbonyl, arylalkoxycarbonyl, heteroaryloxycarbonyl, heteroarylalkoxycarbonyl, alkylcarbonyl, arylcarbonyl, arylalkylcarbonyl, heteroarylcarbonyl and heteroarylalkylcarbonyl, each of which is optionally substituted by one or more substituents independently selected from the group consisting of halogen, hydroxy, cyano, methoxy, amino, nitro, acylamido, thiol, azido, formyl, carboxy and carbonylamido; or R⁸ is:

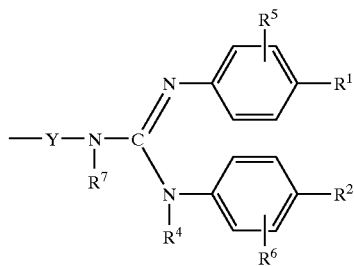

where R¹, R², R⁴, R⁵, R⁶ and R⁷ are defined above and Y is a (C$_{1-6}$)alkylene group, which is optionally substituted by one or more substituents independently selected from the group consisting of (a) halogen, hydroxy, cyano, amino, nitro, acylamido, thiol, azido, formyl, carboxy, carbonylamido and (b) aryl, fused aryl, carbocyclic, heterocyclic, heteroaryl, alkyl, alkenyl, alkynyl, arylalkyl, arylalkenyl arylalkynyl, heteroarylalkyl, heteroarylalkenyl, heteroarylalkynyl, carbocycloalkyl, heterocycloalkyl, acyloxy, alkoxy, alkylthiol, alkoxyalkyl and alkylthioalkyl, each of which is optionally substituted by one or more substituents independently selected from the group consisting of halogen, hydroxy, cyano, methoxy, amino, nitro, acylamido, thiol, azido, formyl, carboxy and carbonylamido;

or R⁷ and R⁸ together form a pyrrolidinyl or piperidinyl ring which is optionally substituted by one or more substituents independently selected from the group consisting of (a) halogen, hydroxy, cyano, amino, nitro, acylamido, thiol, azido, formyl, carboxy, carbonylamido and (b) aryl, fused aryl, carbocyclic, heterocyclic, heteroaryl, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, acyloxy, alkoxy, alkylthiol, alkoxyalkyl, and alkylthioalkyl, each of which is optionally substituted by one or more substituents independently selected from the group consisting of halogen, hydroxy, cyano, methoxy, amino, nitro, acylamido, thiol, azido, formyl, carboxy and carbonylamido;

R⁹ is selected from the group consisting of hydrogen, halogen, hydroxy, cyano, amino, nitro, acylamido, thiol, azido, formyl, carboxy, carbonylamido and:

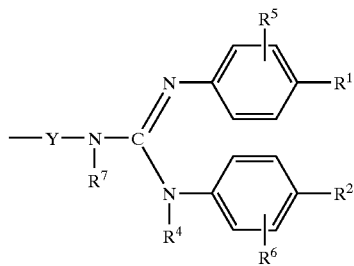

where R¹, R². R⁴, R⁵, R⁶ and R⁷ are defined above;

R¹⁰ is selected from the group consisting of (a) hydrogen and (b) aryl, fused aryl, carbocyclic, heterocyclic, heteroaryl, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, alkoxyalkyl, alkylthioalkyl, COR, CO$_2$R and CONR$_x$R$_y$, each of which is optionally substituted by one or more substituents independently selected from the group consisting of halogen, hydroxy, cyano, methoxy, amino, nitro, acylamido, thiol, azido, formyl, carboxy and carbonylamido, wherein R, R$_x$ and R$_y$ are independently selected from the group consisting of hydrogen, aryl, fused aryl, carbocyclic, heterocyclic, heteroaryl, alkyl, alkenyl, alkynyl, alkoxyalkyl, alkylthioalkyl, arylalkyl, arylalkenyl, arylalkynyl, heteroarylalkyl, heteroarylalkenyl, heteroalkynyl, carbocycloalkyl and heterocycloalkyl; or R$_x$ and R$_y$ are taken together to form a heterocycle, which is optionally substituted by one or more substituents independently selected from the group consisting of halogen, hydroxy, cyano, methoxy, amino, nitro, acylamido, thiol, azido, formyl, carboxy and carbonylamido; or R$^{10}$ is:

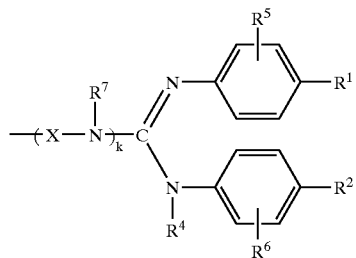

where R$^1$, R$^2$, R$^4$, R$^5$, R$^6$ and R$^7$ are defined above; k is 0 or 1 and X is a (C$_{1-6}$)alkylene group, which is optionally substituted by one or more substituents independently selected from the group consisting of (a) halogen, hydroxy, cyano, amino, nitro, acylamido, thiol, azido, formyl, carboxy, carbonylamido and (b) aryl, fused aryl, carbocyclic, heterocyclic, heteroaryl, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, acyloxy, alkoxy, alkylthiol, alkoxyalkyl and alkylthioalkyl, each of which is optionally substituted by one or more substituents independently selected from the group consisting of halogen, hydroxy, cyano, methoxy, amino, nitro, acylamido, thiol, azido, formyl, carboxy and carbonylamido;

R$^{11}$ is, at each occurrence, independently selected from the group consisting of [(CH$_2$)$_j$—O—]$_j$, (CH$_2$)$_j$—O—(CH$_2$)$_j$—O—(CH$_2$)$_j$ and [(CH$_2$)$_j$—N(R$^7$)—]$_j$—[(CH$_2$)$_j$—O—]$_j$, where j is, at each occurrence, independently 0, 1, 2, 3, 4, 5 or 6, provided that there are no two adjoining oxygens; and the pharmaceutically acceptable salts and esters thereof.

A second aspect of the present invention is directed to pharmaceutical compositions, comprising one or more compounds of Formula I and a pharmaceutically acceptable carrier.

A third aspect of the present invention is directed to novel compounds of formula I:

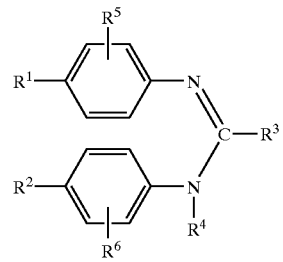

wherein,

R$^1$ and R$^2$ are each independently selected from the group consisting of (a) hydrogen, halogen, hydroxy, cyano, amino, nitro, acylamido, thiol, azido, formyl, carboxy, carbonylamido and (b) aryl, fused aryl, carbocyclic, heterocyclic, heteroaryl, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, acyloxy, alkoxy, alkylthiol alkoxyalkyl and alkylthioalkyl each of which is optionally substituted by one or more substituents independently selected from the group consisting of halogen, hydroxy, cyano, methoxy, amino, nitro, acylamido, thiol, azido, formyl, carboxy and carbonylamido;

R$^3$ is selected from the group consisting of:

—N(R$^7$)—R$^8$,

—N—(CH$_2$)$_m$—O—(CH$_2$)$_m$—O—(CH$_2$)$_m$—R$^9$,
   |
   R$^7$

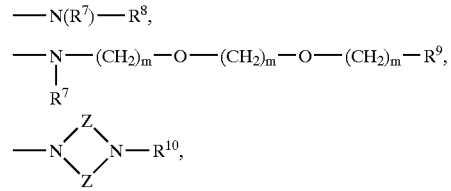

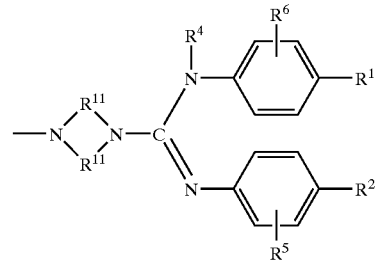

and a 2-amino sugar which is optionally substituted by one or more substituents independently selected from the group consisting of alkyl and alknoyl, and is substituted on the 2-amino nitrogen, where Z is a (C$_{1-6}$)alkylene group, which is optionally substituted by one or more substitutents independently selected from the group consisting of (a) halogen, hydroxy, cyano, amino, nitro, acylamido, thiol, azido, formyl, carboxy, carbonylamido and (b) aryl, fused aryl, carbocyclic, heterocyclic, heteroaryl, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, acyloxy, alkoxy, alkylthiol, alkoxyalkyl and alkylthioalkyl, each of which is optionally substituted by one or more substituents independently selected from the group consisting of halogen, hydroxy, cyano, methoxy, amino, nitro, acylamido, thiol, azido, formyl, carboxy and carbonylamido;

R$^4$ is selected from the group consisting of (a) hydrogen and (b) aryl, fused aryl, carbocyclic, heterocyclic, heteroaryl, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, alkoxyalkyl and alkylthioalkyl, COR, CO$_2$R and CONR$_x$R$_y$, each of which is optionally substituted by one or more substituents selected from the group consisting of halogen, hydroxy, cyano, methoxy, amino, nitro, acylamido, thiol, azido, formyl, carboxy and carbonylamido, wherein R, R$_x$ and R$_y$ are independently selected from the group consisting of hydrogen, aryl, fused aryl, carbocyclic, heterocyclic, heteroaryl, alkyl, alkenyl, alkynyl, alkoxyalkyl, alkylthioalkyl, arylalkyl, arylalkenyl, arylalkynyl, heteroarylalkyl, heteroarylalkenyl, heteroalkynyl, carbocycloalkyl and heterocycloalkyl; or R$_x$ and R$_y$ are taken together to form a heterocycle, which is optionally substituted by one or more substituents independently selected from the group consisting of halogen, hydroxy, cyano, methoxy, amino, nitro, acylamido, thiol, azido, formyl, carboxy and carbonylamido;

R$^5$ and R$^6$ are each zero to four substituents and are independently selected from the group consisting of (a) halogen, hydroxy, cyano, amino, nitro, acylamido, thiol, azido, formyl, carboxy, carbonylamido and (b) aryl, fused aryl, carbocyclic, heterocyclic, heteroaryl, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, acyloxy, alkoxy, alkylthio, alkoxyalkyl and alkylthioalkyl, each of which is optionally substituted by one or more substituents independently selected from the group consisting of halogen, hydroxy, cyano, methoxy, amino, nitro, acylamido, thiol, azido, formyl, carboxy and carbonylamido;

R$^7$ is selected from the group consisting of (a) hydrogen and (b) aryl, fused aryl, carbocyclic, heterocyclic, heteroaryl, alkyl, alkenyl, alkynyl, alkoxyalkyl, alkylthioalkyl, arylalkyl, arylalkenyl, arylalkynyl, heteroarylalkyl, heteroarylalkenyl, heteroarylalkynyl, carbocycloalkyl, heterocycloalkyl, COR, CO$_2$R and CONR$_x$R$_y$, each of which is optionally substituted by one or more substituents independently selected from the group consisting of halogen, hydroxy, cyano, methoxy, amino, nitro, acylamido, thiol, azido, formyl, carboxy and carbonylamido, wherein R, R$_x$ and R$_y$ are independently selected from the group consisting of hydrogen, aryl, fused aryl, carbocyclic, heterocyclic, heteroaryl, alkyl, alkenyl, alkynyl, alkoxyalkyl, alkylthioalkyl, arylalkyl, arylalkenyl, arylalkynyl, heteroarylalkyl, heteroarylalkenyl, heteroalkynyl, carbocycloalkyl and heterocycloalkyl; or R$_x$ and R$_y$ are taken together to form a heterocycle, which is optionally substituted by one or more substituents independently selected from the group consisting of halogen, hydroxy, cyano, methoxy, amino, nitro, acylamido, thiol, azido, formyl, carboxy and carbonylamido;

R$^8$ is selected from the group consisting of aryl, fused aryl, carbocyclic, heterocyclic, heteroaryl, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, aminoalkyl, acyloxy, alkoxy, alkylthio, alkoxyalkyl and alkylthioalkyl, each of which is optionally substituted by one or more substituents independently selected from the group consisting of (a) halogen, hydroxy, cyano, methoxy, amino, nitro, acylamido, thiol, azido, formyl, carboxy, carbonylamido and (b) alkoxycarbonyl, aryloxycarbonyl, arylalkoxycarbonyl, heteroaryloxycarbonyl, heteroarylalkoxycarbonyl, alkylcarbonyl, arylcarbonyl, arylalkylcarbonyl, heteraryl-carbonyl and heteroarylalkylcarbonyl, each of which is optionally substituted by one or more substituents independently selected from the group consisting of halogen, hydroxy, cyano, methoxy, amino, nitro, acylamido, thiol, azido, formyl, carboxy and carbonylamido; or R$^8$ is:

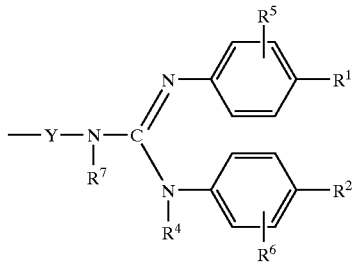

where R$^1$, R$^2$, R$^4$, R$^5$, R$^6$ and R$^7$ are defined above, and Y is a (C$_{1-6}$) alkylene group, which is optionally substituted by one or more substituents independently selected from the group consisting of (a) halogen, hydroxy, cyano, amino, nitro, acylamido, thiol, azido, formyl, carboxy, carbonylamido and (b) aryl, fused aryl, carbocyclic, heterocyclic, heteroaryl, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, acyloxy, alkoxy, alkylthiol, alkoxyalkyl and alkylthioalkyl, each of which is optionally substituted by one or more substituents independently selected from the group consisting of halogen, hydroxy, cyano, methoxy, amino, nitro, acylamido, thiol, azido, formyl, carboxy and carbonylamido;

or R$^7$ and R$^8$ together form a pyrrolidinyl or piperidinyl ring which is optionally substituted by one or more substituents independently selected from the group consisting of (a) halogen, hydroxy, cyano, amino, nitro, acylamido, thiol, azido, formyl, carboxy, carbonylamido and (b) aryl, fused aryl, carbocyclic, heterocyclic, heteroaryl, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, acyloxy, alkoxy, alkylthiol, alkoxyalkyl, and alkylthioalkyl, each of which is optionally substituted by one or more substituents independently selected from the group consisting of halogen, hydroxy, cyano, methoxy, amino, nitro, acylamido, thiol, azido, formyl, carboxy and carbonylamido;

R$^9$ is selected from the group consisting of hydrogen, halogen, hydroxy, cyano, amino, nitro, acylamido, thiol, azido, formyl, carboxy carbonylamido, and

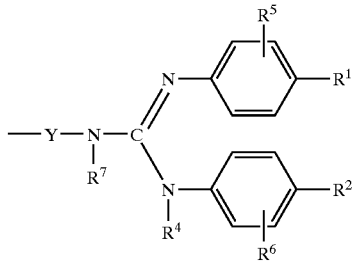

where R$^1$, R$^2$, R$^4$, R$^5$, R$^6$ and R$^7$ are defined above;

R$^{10}$ is selected from the group consisting of (a) hydrogen and (b) aryl, fused aryl, carbocyclic, heterocyclic, heteroaryl, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, alkoxyalkyl, alkylthioalkyl, COR, CO$_2$R and CONR$_x$R$_y$, each of which is optionally substituted by one or more substituents independently selected from the group consisting of halogen, hydroxy, cyano, methoxy, amino, nitro, acylamido, thiol, azido, formyl, carboxy and carbonylamido, wherein R, $R_x$ and $R_y$ are independently selected from the group consisting of hydrogen, aryl, fused aryl, carbocyclic, heterocyclic, heteroaryl, alkyl, alkenyl, alkynyl, alkoxyalkyl, alkylthioalkyl, arylalkyl, arylalkenyl, arylalkynyl, heteroarylalkyl, heteroarylalkenyl, heteroalkynyl, carbocycloalkyl and heterocycloalkyl; or $R_x$ and $R_y$ are taken together to form a heterocycle, which is optionally substituted by one or more substituents independently selected from the group consisting of halogen, hydroxy, cyano, methoxy, amino, nitro, acylamido, thiol, azido, formyl, carboxy and carbonylamido; or $R^{10}$ is:

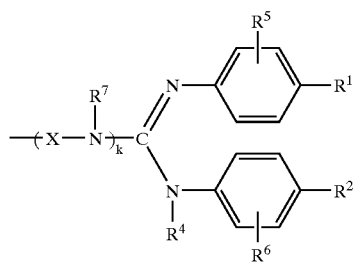

where $R^1$, $R^2$, $R^4$, $R^5$, $R^6$ and $R^7$ are defined above; k is 0 or 1 and X is a $(C_{1-6})$alkylene group, which is optionally substituted by one or more substituents independently selected from the group consisting of (a) halogen, hydroxy, cyano, amino, nitro, acylamido, thiol, azido, formyl, carboxy, carbonylamido and (b) aryl, fused aryl, carbocyclic, heterocyclic, heteroaryl, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, acyloxy, alkoxy, alkylthiol, alkoxyalkyl and alkylthioalkyl, each of which is optionally substituted by one or more substituents independently selected from the group consisting of halogen, hydroxy, cyano, methoxy, amino, nitro, acylamido, thiol, azido, formyl, carboxy and carbonylamido;

$R^{11}$ is, at each occurrence, independently selected from the group consisting of $[(CH_2)_j\text{—}O\text{—}]_j$, $(CH_2)_j\text{—}O\text{—}(CH_2)_j\text{—}O\text{—}(CH_2)$, and $[(CH_2)_j\text{—}N(R^7)\text{—}]_j[(CH_2)_j\text{—}O\text{—}]_j$, where j is, at each occurrence, independently 0, 1, 2, 3, 4, 5 or 6, provided that there are no two adjoining oxygens;

with the proviso that (a) when $R^1$ and $R^2$ are both methyl, $R^3$ is not cyclohexylamino, (b) when $R^1$, $R^2$, $R^5$ and $R^6$ comprise not more than three substitutents other than hydrogen, $R^3$ is not $(C_{1-6})$alkylamino, di$(C_{1-6})$alkylamino, unsubstituted piperazinyl or N-$(C_{1-6})$alkylpiperazinyl and (c) when Y is ethylene, at least one of the group consisting of $R^1$, $R^2$, $R^4$, $R^5$, $R^6$ and $R^7$ is other than hydrogen; and the pharmaceutically acceptable salts and esters thereof.

DETAILED DESCRIPTION OF THE PREFERRED EMBODIMENTS

Figure 1:
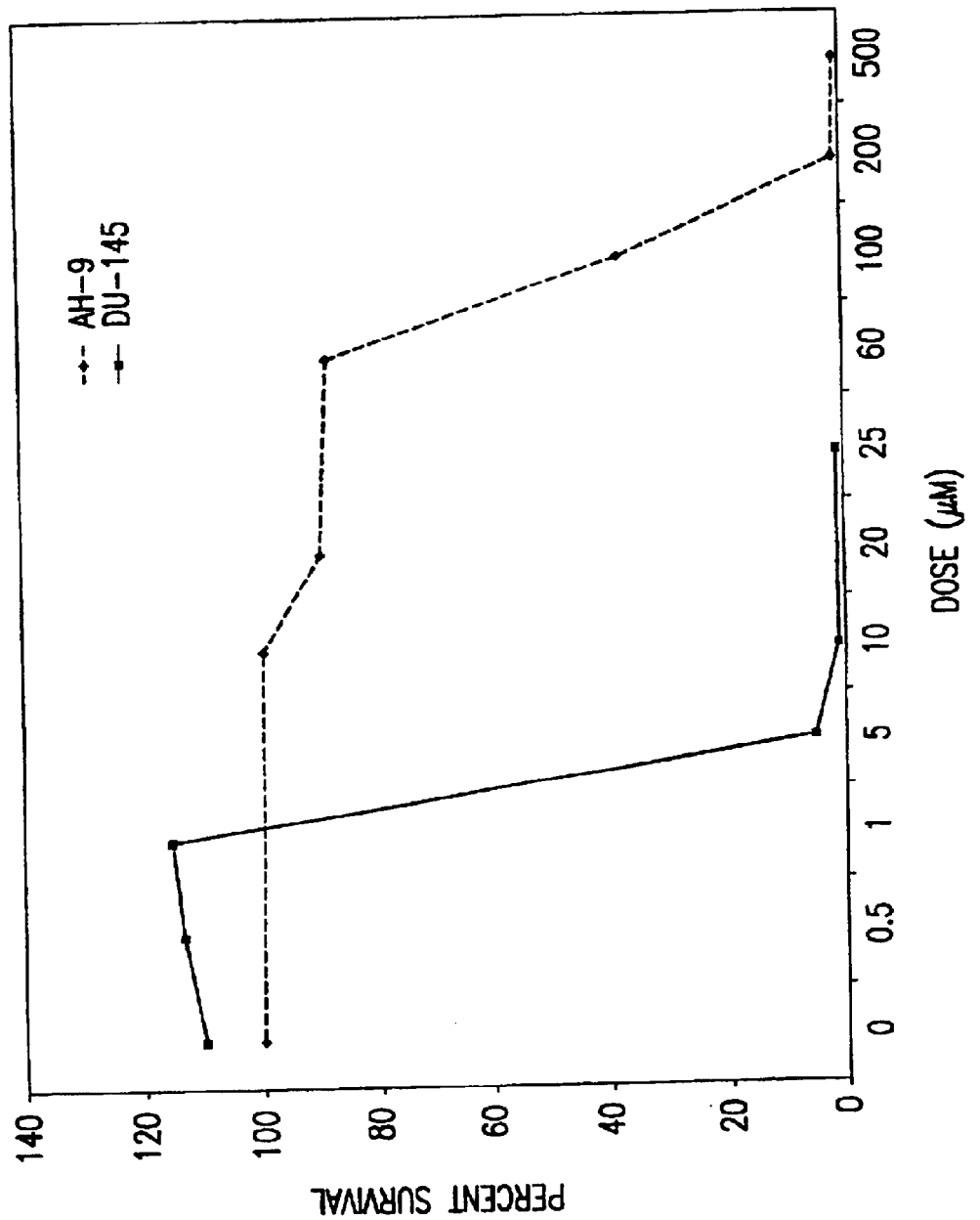
FIG. 1 is a graph which compares the effects of the compound of Example 8 on normal human endothelial cells (AH-9) and human prostate cancer cells (DU145). Cells were exposed to the compound for seven days at the concentrations indicated. Cytotoxicity was assessed using the MTS assay.

The term "alkyl" as employed herein by itself or as part of another group refers to both straight and branched chain radicals of up to 12 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl.

The term "alkenyl" is used herein to mean a straight or branched chain radical of 2–20 carbon atoms, unless the chain length is limited thereto, including, but not limited to, ethenyl, 1-propenyl, 2-propenyl, 2-methyl-l-propenyl, 1-butenyl, 2-butenyl, and the like. Preferably, the alkenyl chain is 2 to 10 carbon atoms in length, more preferably, 2 to 8 carbon atoms in length most preferably from 2 to 4 carbon atoms in length.

The term "alkynyl" is used herein to mean a straight or branched chain radical of 2–20 carbon atoms, unless the chain length is limited thereto, wherein there is at least one triple bond between two of the carbon atoms in the chain, including, but not limited to, acetylene, 1-propylene, 2-propylene, and the like. Preferably, the alkynyl chain is 2 to 10 carbon atoms in length, more preferably, 2 to 8 carbon atoms in length, most preferably from 2 to 4 carbon atoms in length. In all instances herein where there is an alkenyl or alkynyl moiety as a substituent group, the unsaturated linkage, i.e., the vinylene or acetylene linkage is preferably not directly attached to a nitrogen, oxygen or sulfur moiety.

The term "alkoxy" is used herein to mean a straight or branched chain Di radical of 1 to 20 carbon atoms, unless the chain length is limited thereto, bonded to an oxygen atom, including, but not limited to, methoxy, ethoxy, n-propoxy, isopropoxy, and the like. Preferably the alkoxy chain is 1 to 10 carbon atoms in length, more preferably 1 to 8 carbon atoms in length.

The term "aryl" as employed herein by itself or as part of another group refers to monocyclic or bicyclic aromatic groups containing from 6 to 12 carbons in the ring portion, preferably 6–10 carbons in the ring portion, such as phenyl, naphthyl or tetrahydronaphthyl.

The term "heteroaryl" as employed herein refers to groups having 5 to 14 ring atoms; 6, 10 or 14 π electrons shared in a cyclic array; and containing carbon atoms and 1, 2 or 3 oxygen, nitrogen or sulfur heteroatoms (where examples of heteroaryl groups are: thienyl, benzo[β]thienyl, naphtho[2, 3-β]thienyl, thianthrenyl, furyl, pyranyl, isobenzofuranyl, benzoxazolyl, chromenyl, xanthenyl, phenoxathienyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4αH-carbazolyl, carbazolyl, β-carbolinyl, phenanthridinyl, acridinyl, pyrimidinyl, phenanthrolinyl, phenazinyl, isothiazolyl, phenothiazinyl, isoxazolyl, furazanyl and phenoxazinyl groups).

The term "aralkyl" or "arylalkyl" as employed herein by itself or as part of another group refers to $C_{1-6}$alkyl groups as discussed above having an aryl substituent, such as benzyl, phenylethyl or 2-naphthylmethyl.

The term "cycloalkyl" as employed herein by itself or as part of another group refers to cycloalkyl groups containing 3 to 9 carbon atoms. Typical examples are cyclopropyl, cyclobutyl, cyclopentyl, cyclohexyl, cycloheptyl, cyclooctyl and cyclononyl.

The term "halogen" or "halo" as employed herein by itself or as part of another group refers to chlorine, bromine, fluorine or iodine with chlorine being preferred.

The term "aminoalkyl" as employed herein by itself or as part of another group refers to an alkyl group having from 1 to 6 carbon atoms which is substituted with one or more amino groups.

The term "heterocycle" or "heterocyclic ring," as used herein except where noted, represents a stable 5- to 7-membered mono- or bicyclic or stable 7- to 10-membered bicyclic heterocyclic ring system any ring of which may be saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. Especially useful are rings containing one oxygen or sulfur, one to three nitrogen atoms, or one oxygen or sulfur combined with one or two nitrogen atoms. The heterocyclic ring may be attached at any heteroatom or carbon atom which results in the creation of a stable structure. Examples of such heterocyclic groups include piperidinyl, piperazinyl, 2-oxopiperazinyl, 2-oxopiperidinyl, 2-oxopyrrolodinyl, 2-oxoazepinyl, azepinyl, pyrrolyl, 4piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl. Morpholino is the same as morpholinyl.

The pharmaceutically acceptable salts of the compounds of the invention (in the form of water- or oil-soluble or dispersible products) include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, nitrate, oxalate, palmoate, pectinate, persulfate, 3-phenylpropionate, picrate, pivalate, propionate, succinate, sulfate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides: dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides and others. Preferred acids for forming acid addition salts include HCl and acetic acid.

Pharmaceutically acceptable esters of the compounds of the present invention include the alkyl and aralkyl esters of carboxyl containing compounds as well as the alkanoate and aralkanoate esters of hydroxy containing compounds. Preferred alkyl and aralkyl esters include the methyl, ethyl, propyl and butyl esters of carboxyl containing compounds. Preferred alkanoate and aralkanoate esters include the formate, acetate, propionate, butyrate, and phenylacetic esters of hydroxy containing compounds.

The compounds of the present invention are administered in an amount effective to achieve its intended purpose. Exemplary amounts are in the dosage range of about 0.1 to about 500 mg/kg, preferably between 0.1 to 50 mg/kg body weight, using a dosing regime consisting of a single or 24 divided daily doses.

The pharmaceutical compositions of the invention can be administered to any animal that can experience the beneficial effects of the compounds of the invention. Foremost among such animals are humans, although the invention is not intended to be so limited.

The pharmaceutical compositions of the present invention can be administered by any means that achieves their intended purpose. For example, administration can be by oral, parenteral, subcutaneous, intravenous, intramuscular, intraperitoneal, transdermal, buccal, rectal or ocular routes. The pharmaceutical compositions of the present invention may also be administered directly within the postoperative space following the removal of a solid tumor. The compound can be administered alone or in combination with other therapeutic agents or in conjunction with surgery or radiation therapy. The dosage administered will be dependent upon the age, health, and weight of the recipient, any concurrent treatments, frequency of treatment, and the nature of the effect desired.

In addition to the pharmacologically active compounds, the pharmaceutical preparations can contain suitable pharmaceutically acceptable carriers comprising excipients and auxiliaries that facilitate processing of the active compounds into preparations that can be used pharmaceutically.

The pharmaceutical preparations of the present invention are manufactured in a manner that is, itself, known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example, lactose or sucrose, mannitol or sorbitol, cellulose preparations and/or calcium phosphates, for example, tricalcium phosphate or calcium hydrogen phosphate, as well as binders, such as, starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added, such as, the above-mentioned starches and also carboxymethyl-starch, cross-linked polyvinyl pyrrolidone, agar, or alginic acid or a salt thereof, such as, sodium alginate. Auxiliaries are, above all, flow-regulating agents and lubricants, for example, silica, talc, stearic acid or salts thereof, such as, magnesium stearate or calcium stearate, and/or polyethylene glycol. Dragee cores are provided with suitable coatings that, if desired, are resistant to gastric juices. For this purpose, concentrated saccharide solutions can be used, which may optionally contain gum arabic, talc, polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations, such as, acetylcellulose phthalate or hydroxypropylmethyl-cellulose phthalate, are used. Dye stuffs or pigments can be added to the tablets or dragee coatings, for example, for identification or in order to characterize combinations of active compound doses.

Other pharmaceutical preparations that can be used orally include push-fit capsules made of gelatin, as wed as soft, scaled capsules made of gelatin and a plasticizer, such as, glycerol or sorbitol. The push-fit capsules can contain the active compounds in the form of granules that may be mixed with fillers such as lactose, binders such as starches, and/or lubricants such as talc or magnesium stearate and, optionally, stabilizers. In soft capsules, the active compounds are preferably dissolved or suspended in suitable liquids, such as, fatty oils or liquid paraffin. In addition, stabilizers may be added.

Suitable formulations for parenteral administration include aqueous solutions of the active compounds in water-soluble form, for example, water-soluble salts, alkaline solutions and cyclodextrin inclusion complexes. Especially preferred alkaline salts are ammonium salts prepared, for example, with Tris, choline hydroxide, Bis-Tris propane, N-methylglucamine, or arginine. One or more modified or unmodified cyclodextrins can be employed to stabilize and increase the water solubility of compounds of the present invention. Useful cyclodextrins for this purpose are disclosed in U.S. Pat. Nos. 4,727,064, 4,764,604, and 5,024,998.

In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG400). Aqueous injection suspensions can contain substances that increase the viscosity of the suspension, for example, sodium carboxymethyl cellulose, sorbitol, and/or dextran. Optionally, the suspension may also contain stabilizers.

Compounds of the present invention inhibit tumor progression. Thus, the compounds can be employed to treat cancer, in a patient in need thereof. By the term "treatment of cancer" or "treating cancer" is intended description of an activity of compounds of the present invention wherein said activity prevents, alleviates or ameliorates any of the symptoms known in the art to be associated with the pathology commonly known as "cancer." The term "cancer" refers to the spectrum of pathological symptoms associated with the initiation or progression, as well as metastasis, of malignant tumors. By the term "tumor" is intended, for the purpose of the present invention, a growth of tissue that occurs as a consequence of the dysregulation of cell growth, cell cycling, cell division, and/or cell death. As the rate at which a tumor grows depends on these factors, tumorogenesis can occur through either excess proliferation or insufficient cell death. The tumor that is particularly relevant to the invention is the malignant tumor, one in which the primary tumor has the properties of invasion or metastasis or which shows a greater degree of anaplasia than do benign tumors. Thus, "treatment of cancer" or "treating cancer" refers to an activity that prevents, alleviates or ameliorates any of the primary phenomena (initiation, progression, metastasis) or secondary symptoms associated with the disease.

Cancers that are treatable are broadly divided into categories including carcinoma, lymphoma and sarcoma. Examples of carcinomas that can be treated by the composition of the present invention include, but are not limited to: adenocarcinoma, acinic cell adenocarcinoma, adrenal cortical carcinomas, alveoli cell carcinoma, anaplastic carcinoma, basaloid carcinoma, basal cell carcinoma, bronchiolar carcinoma, bronchogenic carcinoma, renaladinol carcinoma, embryonal carcinoma, anometroid carcinoma, fibrolamolar liver cell carcinoma, follicular carcinomas, giant cell carcinomas, hepatocellular carcinoma, intraepidermal carcinoma, intraepithelial carcinoma, leptomanigio carcinoma, medullary carcinoma, melanotic carcinoma, menigual carcinoma, mesometonephric carcinoma, oat cell carcinoma, prostatic carcinoma, squamal cell carcinoma, sweat gland carcinoma, transitional cell carcinoma, and tubular cell carcinoma. Sarcomas that can be treated by the composition of the present invention include, but are not limited to: amelioblastic sarcoma, angiolithic sarcoma, botryoid sarcoma, endometrial stroma sarcoma, ewing sarcoma, fascicular sarcoma, giant cell sarcoma, granulositic sarcoma, immunoblastic sarcoma, juxaccordial osteogenic sarcoma, coppices sarcoma, leukocytic sarcoma (leukemia), lymphatic sarcoma (lympho sarcoma), medullary sarcoma, myeloid sarcoma (granulocitic sarcoma), austiogenci sarcoma, periosteal sarcoma, reticulum cell sarcoma (histiocytic lymphoma), round cell sarcoma, spindle cell sarcoma, synovial sarcoma, and telangiectatic audiogenic sarcoma. Lymphomas that can be treated by the composition of the present invention include, but are not limited to: Hodgkin's disease and lymphocytic lymphomas, such as Burkitt's lymphoma, NPDL NML, NH and diffuse lymphomas.

Cancers that are treatable using compounds described by this invention include but are not limited to solid tumors. Example solid tumors that can be treated by the composition of the present invention include, but are not limited to: solid tumors of the breast, brain, ovary, uterus, prostrate, skin, colorectum, kidney, neuroendocrine system, pancreas and lung.

The compounds of the invention are also useful for treating, preventing and ameliorating pain including neuropathic pain, inflammatory pain, surgical pain and chronic pain. In particular, the compounds of the invention may be used to treat, prevent or ameliorate pain that is the result of surgery, trauma, headache, arthritis, pain associate with terminal cases of cancer, and pain associated with degenerative diseases. The compounds of the present invention may also be used to treat phantom pain that results from the amputation of an extremity.

The following examples are illustrative, but not limiting, of the method and compositions of the present invention. Other suitable modifications and adaptations of the variety of conditions and parameters normally encountered and obvious to those skilled in the art are within the spirit and scope of the invention.

EXAMPLES

Example 1

Preparation of 1-[(N,N'-Di-p-tolyl)amidino]-4-methyl-piperizine 1.05 mmol of 1-methylpiperazine was dissolved in 10 ml of N,N'-dimethylformamide (DMF), and 1.0 mmol of 1,3-di-p-tolylcarbodiimide was added. After 0.5 h. of stirring at room temperature, a small precipitation was removed by filtration and washed twice with 1 ml of DMF. The filtrates were collected and kept at room temperature overnight. 50 ml of water was added to the solution. An oil precipitated after 0.5 h which transformed into a solid. The solid residue was collected by filtration, washed twice with water and dissolved in 20 ml of methanol. 0.2 ml of conc. HCl was added was added to the methanol solution. After evaporation of the methanol, the residue was redissolved in methanol, and pure product was precipitated from the solution with ethyl ether. Yield=78%.

Example 2

Preparation of 1-[(N,N'-Di-p-tolyl)amidino] piperizine 1.2 mmol of piperazine was dissolved in 10 ml of DMF and 1.0 mmol of 1,3-di-p-tolylcarbodiimide was added. After 0.5 hour of stirring at room temperature, a small precipitation was filtered off, and washed twice with 1 ml of DMF. The filtrates were collected and kept at room temperature overnight. 50 ml of water was added to the solution. A precipitated oil was separated by centrifugation. The residual oil was dissolved in 10 ml of methanol and 0.2 ml of conc. HCl was added. The methanol solution was concentrated to 2 ml and purified by gel filtration on Sephadex LH-20 in methanol. Yield=52%.

Example 3

Preparation of 1,4-Di-[(N,N'-di-p-tolyl)amidino] piperizine 0.5 mmol of piperazine was dissolved in 10 ml of DMF and 1.05 mmol of 1,3 di-p-tolylcarbodiimide was added. After 0.5 h. of stirring at room temperature, a small precipitation was filtered off and washed twice with 1 ml of DMF. The filtrates were collected and kept at room temperature overnight. To the DMF solution, 50 ml of water was added. The precipitated solid was filtered and washed with water. The solid was dissolved in ethyl acetate (20 ml) and 0.2 ml of conc. HCl conc. was added. The product began to precipitate within 15 min. After 1 hour, the precipitate was filtered and washed with ethyl ether. Yield=76%.

Example 4

Preparation of 1-Amino-4-[(N,N'-di-p-tolyl) guanidinyl]butane

The title compound was prepared according to Example 2 using 1,4-diaminobutane in place of piperazine. Yield of pure compound=48%.

Example 5

Preparation of 1,4-Di-[(N,N'-di-p-tolyl)guanidinyl] butane

The title compound was prepared according to Example 3 using 1,4-diaminobutane in place of piperazine. Yield of pure compound=82%.

Example 6

Preparation of (S)-(−)-1-[(N,N'-Di-p-tolyl) guanidinyl]-1-phenylethane

The title compound was prepared according to Example 1 using (S)-(−)-α-methylbenzylamine in place of methylpiperazine. Yield of pure compound=77%.

Example 7

Preparation of (R)-(+)-1-[(N,N'-Di-p-tolyl) guanidinyl]-1-phenylethane

The title compound was prepared according to Example 1 using (R)(+)-α-methylbenzylamine in place of methylpiperazine. Yield of pure compound=79%.

Example 8

Preparation of 1-[(N,N'-Di-p-tolyl)amidino]-(trans-1'-cinnamyl)piperizine

To a solution of 10 mmol of trans-1-cinnamylpiperazine in 40 ml of DMF was added 1 mmol of N-diisopropylethylamine followed by 10 mmol of 1,3-ditolylcarbodiimide at room temperature. A precipitate was formed which was filtered off. 100 ml of water was added to the filtrate. The precipitated white solid was filtered off and washed with water. After drying, the compound was dissolved in 200 ml of boiling 2-propanol containing 1.5 ml of concentrated HCl. After cooling, the precipitated crystalline product was filtered off. Yield: 95% of pure product. $R_f$ (TLC)=0.54 (n-butanol, acetic acid, water; 3:1:1). The structure of the product was confirmed by mass spectrometry and X-ray analysis.

Example 9

Preparation of 1-[(N,N'-di-p-tolyl)guanidinyl]-2-(3-indolyl)ethane

The title compound was prepared according to the method of Example 1, using tryptamine in place of methylpiperazine. Yield of pure compound=87%.

Example 10

Preparation of Benzyl 2-[(N,N'-Di-p-tolyl)guanidinyl]-3-(3-indolyl)propionate 1.0 mmol of tryptophan benzyl ester hydrochloride was dissolved in 20 ml of DMF and 1.1 mmol of diisopropylethylamine was added. After 10 min, 1.0 mmol of 1,3 di-p-tolylcarbodiimide was added to the stirred solution. The reaction mixture was stirred overnight in room temperature. The precipitated solid was filtered off and washed twice with 1 ml of DMF. To the collected filtrate, 50 ml of water was added. The precipitated solid was collected by filtration and washed with water. The solid was dissolved in ethyl acetate and 0.1 ml of conc. HCl was added. The pure product was precipitated from the solution with ethyl ether. Yield of pure compound=79%.

Example 11

Preparation of Methyl 2-[(N,N'-Di-p-tolyl)guanidinyl]-3-(3-indolyl)propionate

The title compound was prepared according to Example 10 using tryptophan methyl ester hydrochloride in place of tryptophan benzyl ester hydrochloride. Yield of pure compound=72%.

Example 12

Preparation of (N,N'-Di-p-tolyl)guanidinylcyclohexane

The title compound was obtained according to Example 1 using cyclohexylamine in place of methylpiperazine. Yield of pure compound=82%.

Example 13

Preparation of 1-[(N,N'-Di-p-tolyl)guanidinyl]pyrrolidine

The title compound was prepared according to Example 10 using 1-aminopyrrolidine hydrochloride in place of tryptophan benzyl ester hydrochloride. Yield of pure compound=68%.

Example 14

Preparation of 4-Cyano-1-[(N,N'-di-p-tolyl)amino]-4-phenylpiperidine

The title compound was prepared according to Example 10 using 4-cyano-4-phenylpiperidine hydrochloride in place of tryptophan benzyl ester hydrochloride. Yield of pure compound=82%.

Example 15

Preparation of 1,12-Di-(N,N'-di-p-tolyl)guanidinyl]-4,9 dioxa-dodecane

The title compound was prepared according to Example 3 using 4.9-dioxa-1,12-dodecanediamine in place of piperazine. Yield of pure compound=75%.

Example 16

Preparation of 7,16-Di-[(N,N'-Di-p-tolyl)amidino]-1,4,10,13-tetraoxa-7,16-diazacyclooctadecane The title compound was prepared according to Example 3 using 1,4,10,13-tetraoxa-7,16-diazacyclooctadecane in place of piperazine. Yield of pure compound=77%.

Example 17

Preparation of 2-[(N,N'-Di-p-tolyl)guanidinyl]benzothiazole

The title compound was prepared according to Example 1 using 2-aminobenzothiazole in place of methylpiperazine. Yield of pure compound=68%.

Example 18

Preparation of Methyl 2-[(N,N'-Di-p-tolyl)guanidinyl]-4-methylvalerate

The title compound was prepared according to Example 10 using D-leucine methyl ester hydrochloride in place of tryptophan benzyl ester hydrochloride. Yield of pure compound=77%.

Example 19

Preparation of Methyl 2-[(N,N'-Di-p-tolyl)guanidinyl]-4-methylthiobutyrate

The title compound was prepared according to Example 10 using methionine methyl ester hydrochloride in place of tryptophan benzyl ester hydrochloride. Yield of pure compound=74%.

Example 20

Preparation of 1-Amino-2-[(N,N'di-p-tolyl)guanidinyl]ethane

The title compound was prepared according to Example 2 using diaminoethane in place of piperazine. Yield of pure compound=47%.

Example 21

Preparation of 1,2-Di-[(N,N'-di-p-tolyl)guanidinyl]ethane

The title compound was prepared according to Example 3 using diaminoethane in place of piperazine. Yield of pure compound=88%.

Example 22

Preparation of N-[(N N'-Di-p-tolyl)amidino]glucosamine 1.0 mmol of glucosamine hydrochloride was suspended in DMF (20 ml) and 1.1 mmol of diisopropylethylamine was added. After 0.5 h, 1.0 mmol of 1,3-di-p-tolylcarbodiimide was added. The reaction mixture was stirred overnight at room temperature. The precipitate was removed by filtration and washed with 1 ml of DMF. To the filtrate, 0.1 ml of conc. HCl was added. The product was then precipitated from the DMF solution with ethyl ether. Yield of pure compound= 65%.

Example 23

Preparation of 4(4-Chlorophenyl)-1-[(N,N'-di-p-tolyl)amidino]-4-hydroxypiperidine The title compound was prepared according to Example 10 using 4-(4-chloro)-4hydroxypiperidine hydrochloride in place of tryptophan benzyl ester hydrochloride. Yield of pure compound=73%.

Example 24

Formulation of 1-[(N,N'-Di-p-tolyl)amidino-]-4-(trans-1'-cinnamyl)piperizine β-Cyclodextrin Complex 5 mmol of the compound of Example 8 was dissolved in a stirred, boiling solution of 5 mmol β-cyclodextrin in 80 ml water. The solution was cooled and lyophilized. The lyophilized complex was soluble in water and saline solution at room temperature.

Example 25

Formulation of 1-[(N,N'-Di-p-tolyl)amidino]-4-(trans-1-cinnamyl)piperizine Dextrin Complex 5 mmol of the compound of Example 8 was dissolved in a stirred, boiling solution of 2 g dextrin in 80 ml of water. The solution was spray dried at 120° C. The resulting powder was soluble in water and saline solution at room temperature.

Example 26

In Vitro Activity Against Human Tumor Cell Lines

The KDS series is a collection of novel small molecular weight synthetic organic compounds that are based on the molecular template of cinnarizine, a drug that is currently in clinical use and acts as an antagonist of the neuropeptide, substance P. In addition to its role in the transmission of pain, substance P causes contraction of gastrointestinal smooth muscle and functions to modulate inflammatory and immune responses. Recent reports also suggest that cancers of the lung (Cuttitta, F., et al., *Nature* 316:823 (1985); Moody, T. W., et al., *Life Sci.* 37:105 (1985); Sethi, T., et al., *Cancer Res.* 52:2737s (1992); Siegfried, J. M., et al., *J. Biol. Chem.* 269:8596 (1994); Hennig, I. M., et al., *Int. J. Cancer* 61:786 (1995); Tallett, A., et al., *Peptides* 17:665(1996)), pancreas (Hennig, I. M., et al., *Int. J. Cancer* 61:786 (1995); Bruckner, H. W., et al., *Proc. Ann. Meet. Am. Assoc. Cancer Res.* 34:A1159 1993 (1993)), ovary (Skrabanek, P., et al., *J. Clin. Pathol.* 33:160 (1980); Jekunen, A. P., et al., *Proc. Ann. Meet. Am. Assoc. Cancer Res.* 33:A516 1992 (1992)), and prostate (Pinski, J., et al., *Int. J. Cancer* 55:963 (1993); Han, K., et al., *Prostate* 31:53 (1997); Wasilenko, W. J., et al., *Prostate* 30:167 (1997): Nagakawa, O., et al., *Cancer Lett.* 133:27 (1998)) express receptors to substance P and a related family of neuropeptides and appear to utilize these factors to promote cell survival and induce proliferation.

Based on the in vitro and in vivo tumoricidal activity of cinnarizine a second generation of anti-cancer agents has been synthesized using cinnarizine as a molecular template. These compounds have been subjected to an in vitro cytotoxicity screen.

To date, 31 different analogues in the series have been tested for their cytotoxicity against human prostate, pancreas and breast cancer cells grown in culture. In these experiments, cells were seeded at 400 cells per well 24 hours prior to addition of the test compound. Cells were grown at 37° C. in a humidified atmosphere of 95% air, 5% $CO_2$ for 7 days with daily media changes. Cytotoxicity was assessed using the CellTiter 96 Aqueous Proliferation Assay (Promega, Madison, Wis.). In this assay the conversion of MTS-tetrazolium by metabolically active cells creates a stable colored compound, that can be measured spectrophotometrically at 490 nm.

Cytotoxicity was observed in all three tumor-types at concentrations in the high nanomolar to low micromolar range (Table 1). This observation is particularly important as both prostate and pancreatic cancers are generally reported to be resistant to chemotherapy. Furthermore, the cytotoxic activities of these KDS series compounds were comparable to the cytotoxic activities of doxorubicin, etoposide and vinblastine, three chemotherapeutic agents that are widely used clinically.

TABLE 1

| | Cell Survival | | |
|---|---|---|---|
| | ED 50 ($\mu$M) | | |
| Example No. | Prostate | Breast | Pancreas |
| Cinnezarine | 8.5 | 2.8 | 2.2 |
| 9 | 5.1 | 4.2 | 0.5 |
| 8 | 1.3 | 2.3 | 1.8 |
| 4 | 2.5 | 1.7 | 0.2 |
| 5 | 0.7 | 0.3 | — |
| 14 | 10.8 | 4.6 | — |
| 15 | 2.5 | 0.9 | — |
| 16 | 1.0 | 0.6 | — |
| Doxorubicin | 7.0 | 2.0 | 0.3 |
| Etoposide | 0.6 | 0.4 | 2.0 |
| Vinblastine | 4.0 | 1.2 | 0.2 |
| Estramustine | 11.0 | — | — |

ED50($\mu$M): Effective dose causing death to 50% of cells.

The data shown in Table 1 indicates that seven compounds have significant cytotoxicity activity against a spectrum of human tumors, including the hormone-independent prostate cancer cell line DU145, breast cancer cell line HS578T, and pancreas cancer cell line HS766T.

In a separate experiment (FIG. 1), normal human endothelial cells (AH-9) and human prostate cancer cells (DU145) were exposed to increasing concentrations of the compound of Example 8 for seven days. In contrast to the cancer cells where the compound of Example 8 causes significant cytotoxic activity with an $EC_{50}$ of 3.4 $\mu$M, AH-9 cells were resistant to the effects of the drug with an $EC_{50}$ of 95 $\mu$M. These data suggest that this series of compounds selectively targets cancer cells.

Example 27

In Vivo Efficacy

Based on the results of the in vitro cytotoxicity studies, the compound of Example 8 was selected for evaluation in two in vivo tumor models. This compound exhibits significant antitumor activity when tested against pancreatic and prostate cancer cell lines grown in the mouse sub-renal capsule producing greater than 95% inhibition of tumor growth with no apparent toxicity. The compound was also active when administered to nude mice bearing human prostate cancer xenografts.

The In Vivo Sub-renal Capsule Assay

Figure 2A:
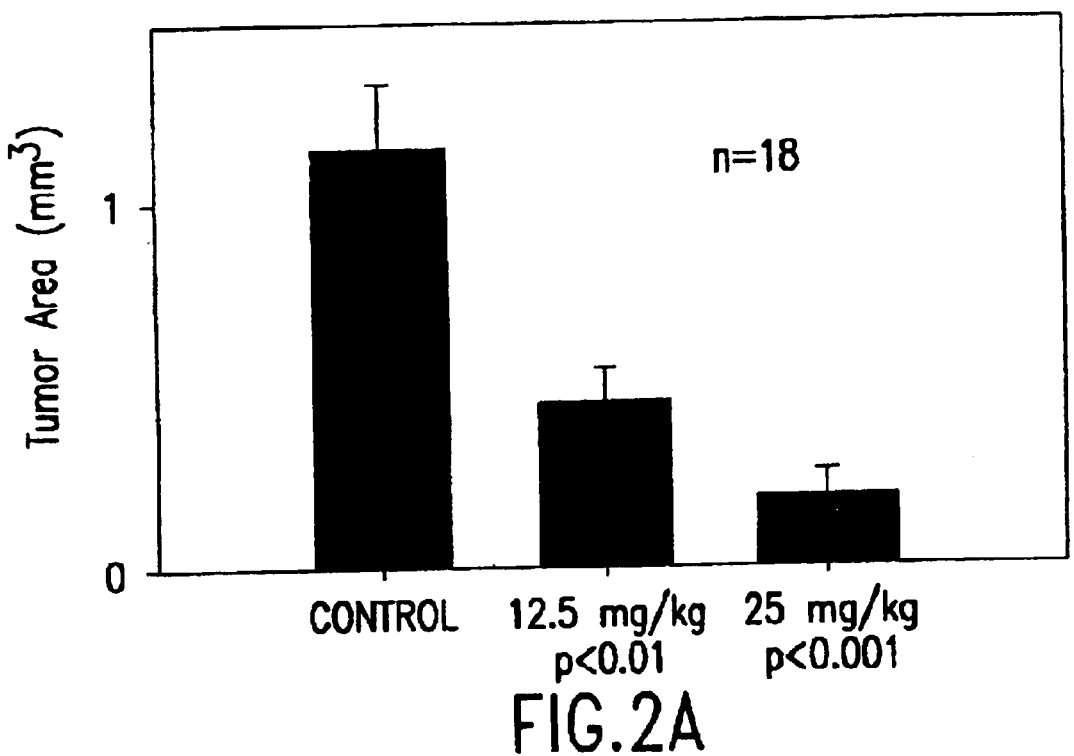
FIG. 2A is a bar graph which depicts the effect of the compound of Example 8 (1-[N,N'-di-p-tolyl)amidino]-4-(trans-1'-cinnamyl)piperizine) on human prostate cancer in BDF/1 mice using the sub-renal capsule assay.
Figure 2B:
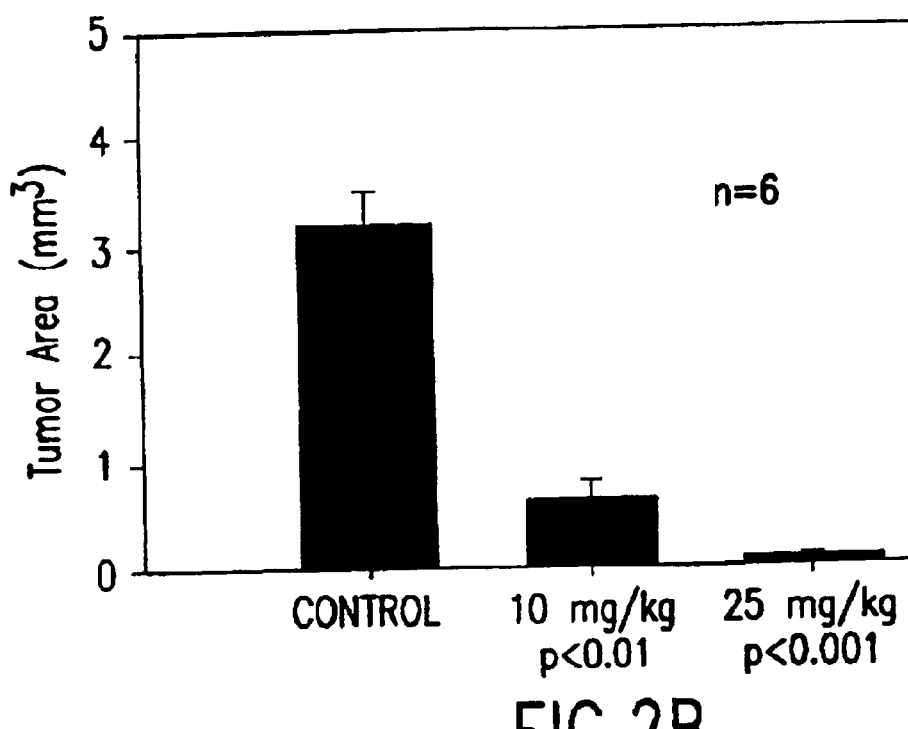
FIG. 2B is a bar graph which depicts the effect of the compound of Example 8 on human pancreatic cancer in BDF/1 mice using the sub-renal capsule assay.

Human cancer cells can be grown in the sub-renal capsule of immuno-competent mice where, for a limited period of time, they escape detection by the mouse's immune system. Thus, the sub-renal capsule assay provides a convenient system to study the effect of drugs on the growth of tumor cells in vivo (Bogden, A. E., et al., *Exp. Cell Biol.* 47:281 (1979)). Briefly, female BDF mice weighing 18–20g were anesthetized, the left kidney exteriorized and a small nick was made in the kidney capsule for implantation of tumor cells. Approximately $1\times10^6$ human prostate (DU14) or pancreatic cancer (HS766T) cells were prepared as a fibrinogen-jelled pellet (Stratton, J. A., et al., *Gynecol. Oncol.* 19:336 (1984); Stratton, J. A., et al., *Gynecol. Oncol.* 30:416 (1988)) and implanted beneath the renal capsule. The compound of Example 8 was administered for five days by daily intraperitoneal injection beginning the day after implantation. One day after the final injection, the animals were killed and the tumor volume was measured. Tumor growth was determined by subtracting the initial size of the implant from the size of the implant size following treatment (Stratton, J. A., et al., *Gynecol Oncol.* 19:336 (1984); Stratton, J. A., et al., *Gynecol. Oncol.* 30:416 (1988)). In these experiments, the compound of Example 8 produced a dose-dependent and highly significant inhibition of tumor growth in both sets of animals (FIGS. 2A and 2B). There was no evidence of systemic toxicity in animals treated with the highest dose (25 mg/kg), of the compound of Example 8 and the tumors were extremely small and, in some cases, undetectable.

Anti-Tumor Activity in Athymic Mice Bearing DU145 Prostate Carcinoma

DU145 tumor cells were injected subcutaneously into the flank of male nude mice (day 0). Palpable tumors develop within 14 days at which time the animals were treated for two weeks with daily intraperitoneal injections of either the compound of Example 8 or the control vehicle. Tumors were measured every two days and volume of tumor was calculated using the formula:

Tumor volume=length×(width)×0.4

Figure 3:
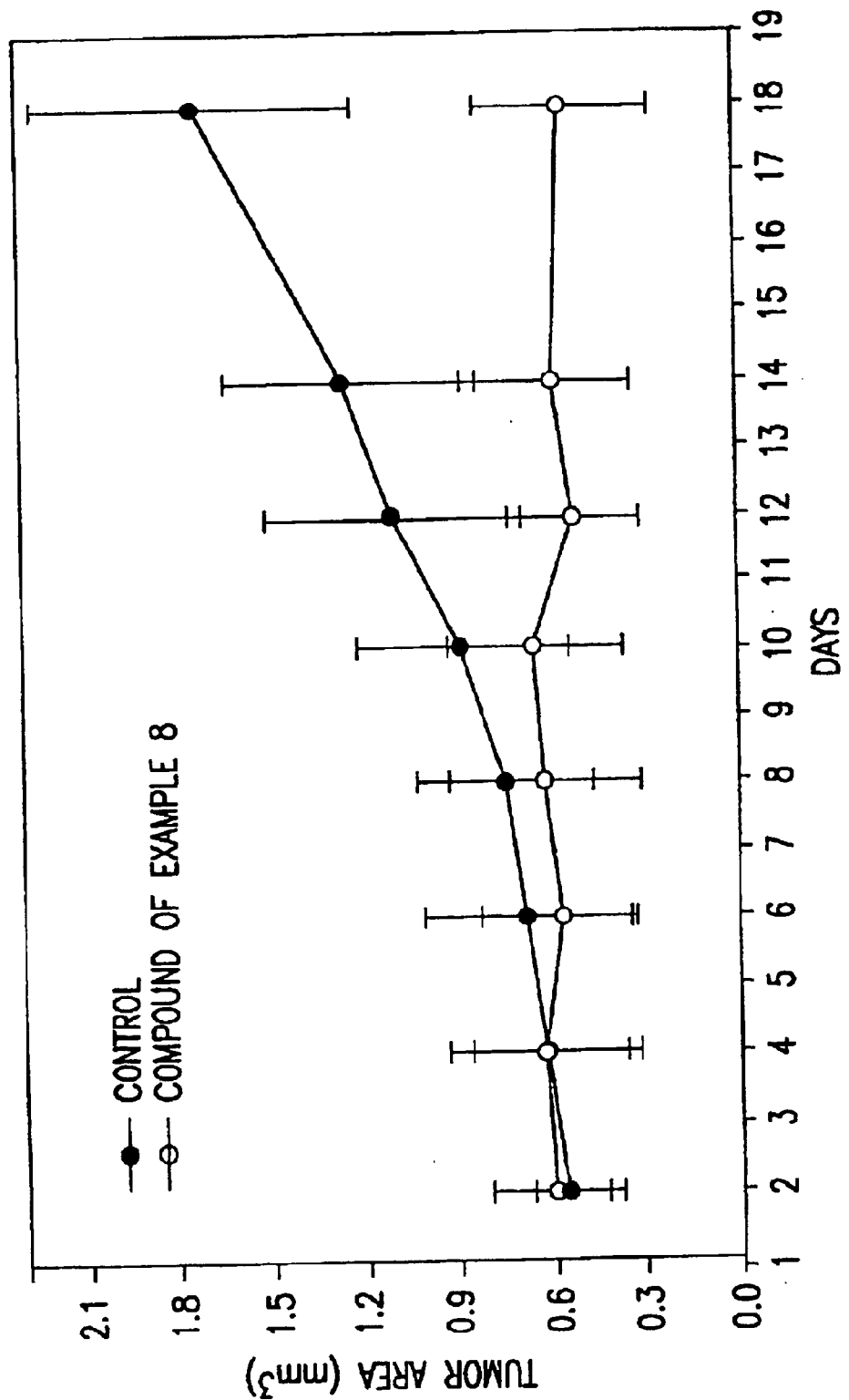
FIG. 3 is a graph showing the effect of the compound of Example 8, at a dose of zero mg/kg (filled circles) and at a dose of 12.5 mg/kg (open circles), on human prostate cancer xenographs in BALB/C/NU mice.

At the end of the study, tumors in control mice had nearly tripled in size. In contrast, tumors grown in mice treated with 12.5 mg/kg/d of the compound of Example 8 failed to grow and were significantly smaller than those grown in control mice (FIG. 3).

Mechanism of Action

The KDS series of compound were designed based on the hypothesis that they would induce apoptosis by blocking the action of neuropeptides and would therefore exhibit cytoreductive activity. To test this hypothesis, human prostate cancer cells were exposed to the compound of Example 8 and examined for evidence of apoptosis. Three pieces of evidence strongly support the role of apoptosis in the cytotoxicity induced by these compounds. First, flow cytometric analysis of cancer cells treated with the compound of Example 8 using terminal deoxynucleotide transferase-mediated dUTP-biotin nick-end labeling TUNEL) revealed a pattern of DNA fragmentation characteristic of apoptosis. Second, mitochondrial transmembrane potential as measured by FACS analysis of the sequestered fluorescent cations JC-1 was reduced in cancer cells exposed to the compound of Example 8. Third, western blots of treated cells revealed the enzymatic cleavage and activation of the caspase 3 proenzyme, a cell death effector.

DNA Fragmentation

Figure 4C:
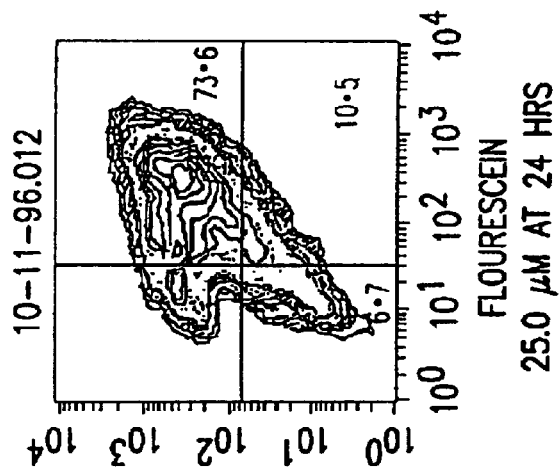
FIGS. 4A–4C illustrate the effects of compound of Example 8 on HS578-T breast carcinoma cells. Cells were exposed to the compound at zero $\mu$M (FIG. 4A), 12.5 $\mu$M (FIG. 4B) or 25 $\mu$M (FIG. 4C) for 24 hours, and the degree of DNA fragmentation measured by flow cytometry using the TUNEL assay.
Figure 4B:
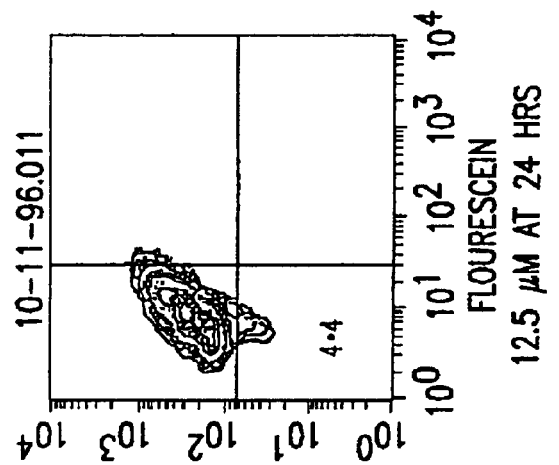
Figure 4A:
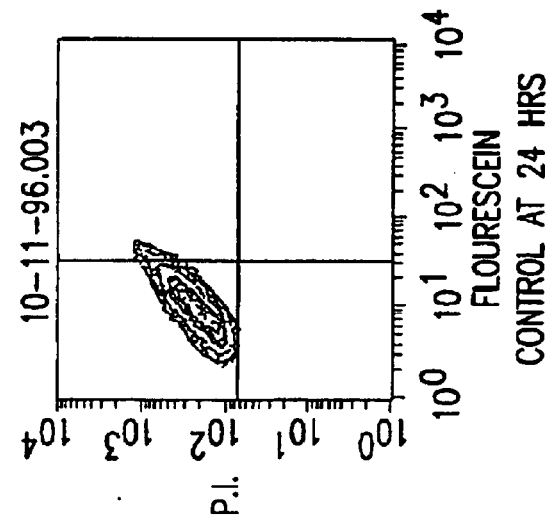
Figure 5A:
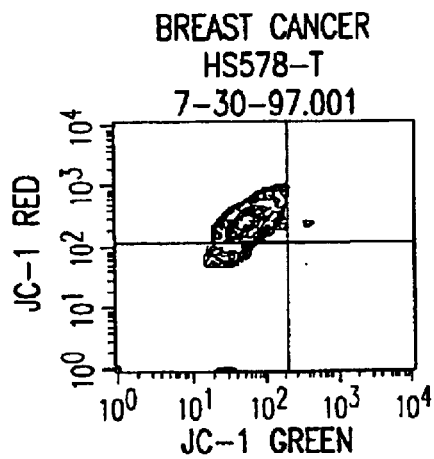
FIGS. 5A–5C illustrate the effects of the compound of Example 8 on human breast cancer cells (HS578-T). Mitochondrial membrane depolarization was assessed by flow cytometry as measured by the fluorescence of cation, JC-1. Cells were exposed to 25 $\mu$M of the compound and fluorescence measured at: 0 hours (FIG. 5A), 2 hours (FIG. 5B) and 5 hours (FIG. 5C).
Figure 5D:
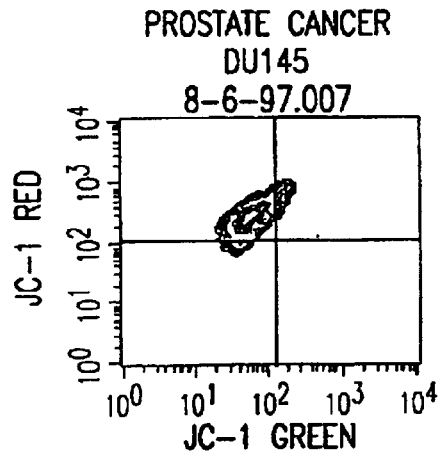
FIGS. 5D–5F illustrate the effects of compound of Example 8 on human prostate cancer cells (DU145). Mitochondrial membrane depolarization was assessed by flow cytometry as measured by the fluorescence of cation, JC-1. Cells were exposed to 25 $\mu$M of the compound and fluorescence measured at: 0 hours (FIG. 5D), 2.5 hours (FIG. 5E) and 4.5 hours (FIG. 5F).
Figure 5B:
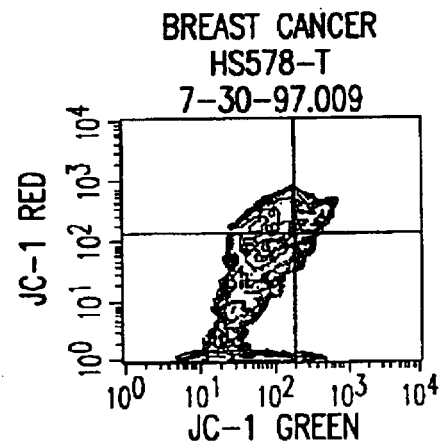
Figure 5E:
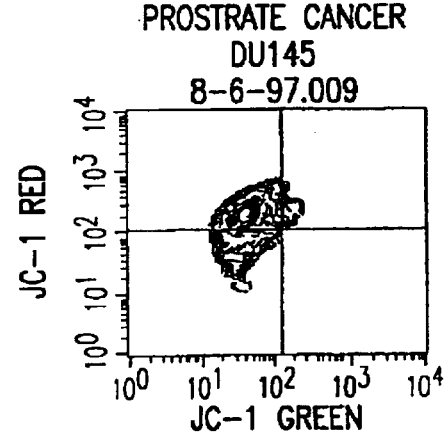
Figure 5C:
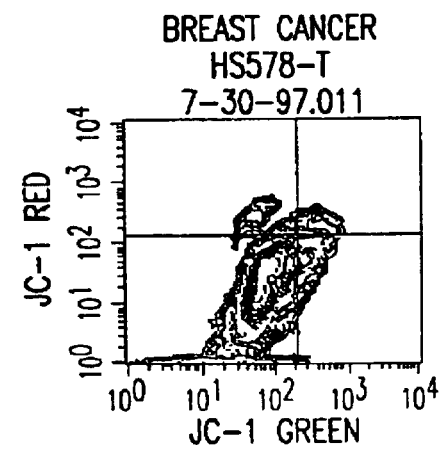
Figure 5F:
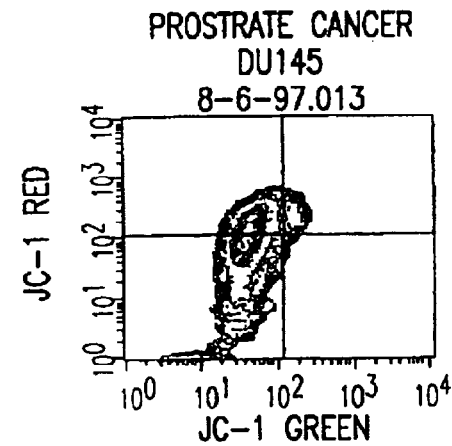

The TUNEL assay examines DNA fragmentation using flow cytometry to detect DNA that is labeled with fluorescein dUTP compared to the total nuclear DNA content of the cell as measured using propidium iodide. A representative experiment is shown in FIGS. 4A–4C. Human HS578T breast cancer cells were treated with either 12.5 or 25 $\mu$M of the compound of Example 8 for 24 hours. As cells undergo apoptosis, DNA fragmentation occurs in a relatively intact nucleus, giving rise to a higher fluorescent intensity (x-axis) with stable staining by propidium iodide (y-axis). Cells undergoing death by necrosis would generally exhibit a low index of propidium iodide (PI) staining as the nucleus degrades.

Effect of the Compound of Example 8 on the Mitochondrial Membrane Potential

Mitochondrial membrane depolarization is an early event in apoptosis. Recent studies have indicated that upon induction of apoptosis, mitochondria lose the ability to sequester charged cations and release the caspase activator protein, cytochrome c from internal stores (Kluck, R. M., et al., *Science* 275:1132 (1997); Yang, J., et al., *Science* 275:1132 (1997)). These early changes in mitochondrial function can be detected using a fluorescent cation, JC-1, that emits a red color when sequestered in the mitochondria of healthy cells, or a green color when localized to the cytoplasm. Cells undergoing apoptosis do not sequester JC-1 in the mitochondria and exhibit a green-fluorescence when analyzed by flow cytometry.

Human breast (HS578-T) and prostate (DU145) cancer cells were exposed to 25 $\mu$M of the compound of Example 8 for varying lengths of times. Both cell lines lost the capacity to sequester JC-1 in the mitochondrial compartment as indicated by a time-dependent increase in green vs. red fluorescence (FIGS. 5A–5F). In an attempt to better quantitate the results of these experiments, the scans were divided into quadrants. At time 0, greater than 90% of the dye was localized in the mitochondria in both breast and prostate cancer cells. By five hours following drug exposure, the mitochondria from the prostate and breast cells contained only 33% and 22% of the dye, respectively.

Caspase-3 Activation

Figure 6:
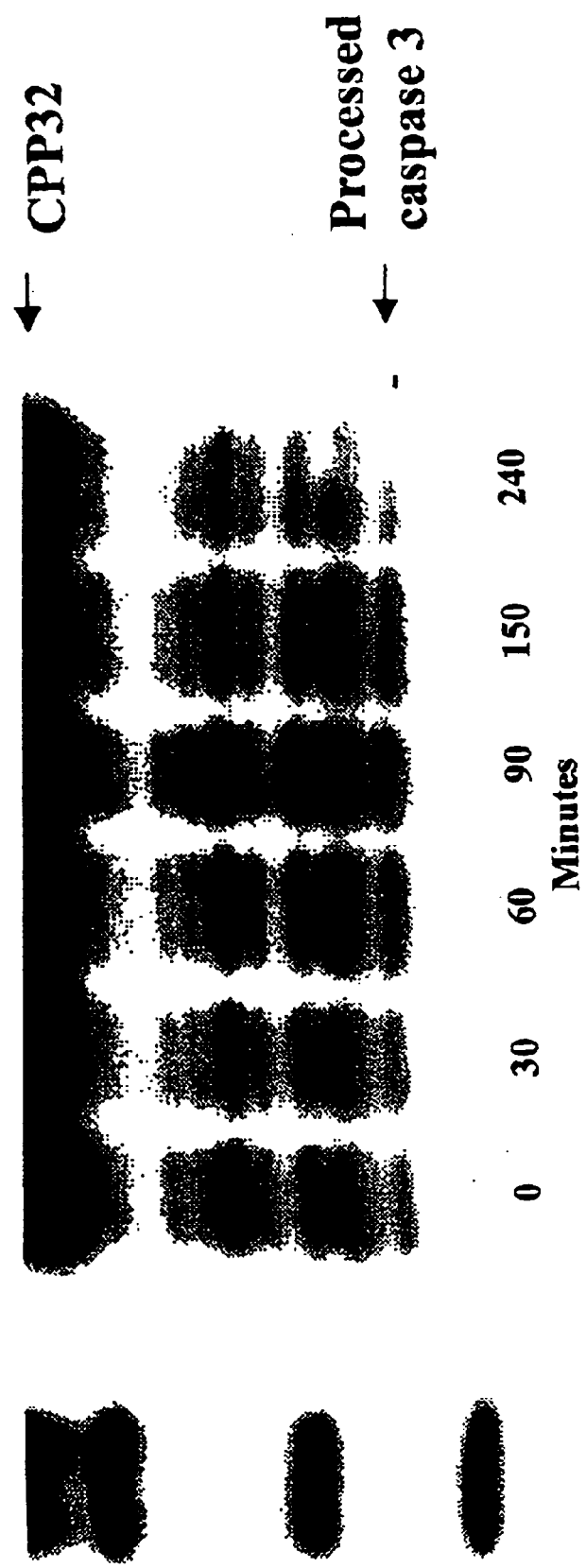
FIG. 6 is an immunoblot illustrating the activation of caspase 3 in human breast cancer cells (HS578-T) exposed to 25 $\mu$M of the compound of Example 8. Cells were exposed to the compound for 0, 30, 60, 90, 150, and 240 minutes of treatment with peak activity occurring 90 minutes after drug addition.

When cells are induced to undergo apoptosis the cell death effector, caspase-3 (CPP-32), is cleaved and activated by proteolytic enzymes. Western blot analysis of the cytosolic fractions of breast cancer cells exposed to 25 $\mu$M of the compound of Example 8 revealed a time-dependent increase in processed caspase-3 (activated caspase-3) with a peak effect occurring 90 minutes after drug exposure (FIG. 6).

DNA fragmentation, changes in mitochondrial permeability, and the cleavage and activation of caspase-3 provide compelling evidence that apoptosis is the primary mechanism through which the KDS series of compounds induces its antitumor effects. Based on these data, it is believed that these compounds are blocking a cell survival signal that is mediated through one or more neuropeptide receptors.

Example 28

Mouse Formalin Test Pain Model.

The formalin test was conducted using standard procedures (Hunskaar et al., *J. Neurosci. Meth.* 14:69–76 (1985). Mice (male CF-1, 20–25 g) were placed in Plexiglass jars for at least 1 hr to accommodate to the environment The animals received either test drug at 5–50 mg/kg p.o. or the appropriate volume of vehicle (normal saline). Thirty minutes after p.o. dosing mice were injected with formalin (20 µl of 2.5% formaldehyde solution in saline) into the dorsal surface of the right hind paw. Mice were observed for behavior in 5 min. intervals for 1 hr after formalin injection.

All experiments were done in a blinded manner. The late phase of the formalin response was measured as licking/biting from 10–50 minutes after formalin injection. Differences between groups were analyzed by one-way analysis of variance (ANOVA), A P value $\leq 0.05$ was considered significant. Reduction in the time spent licking/biting in the late phase of the formalin response is considered an indication of a reduction in chronic pain.

Results

Figure 7:
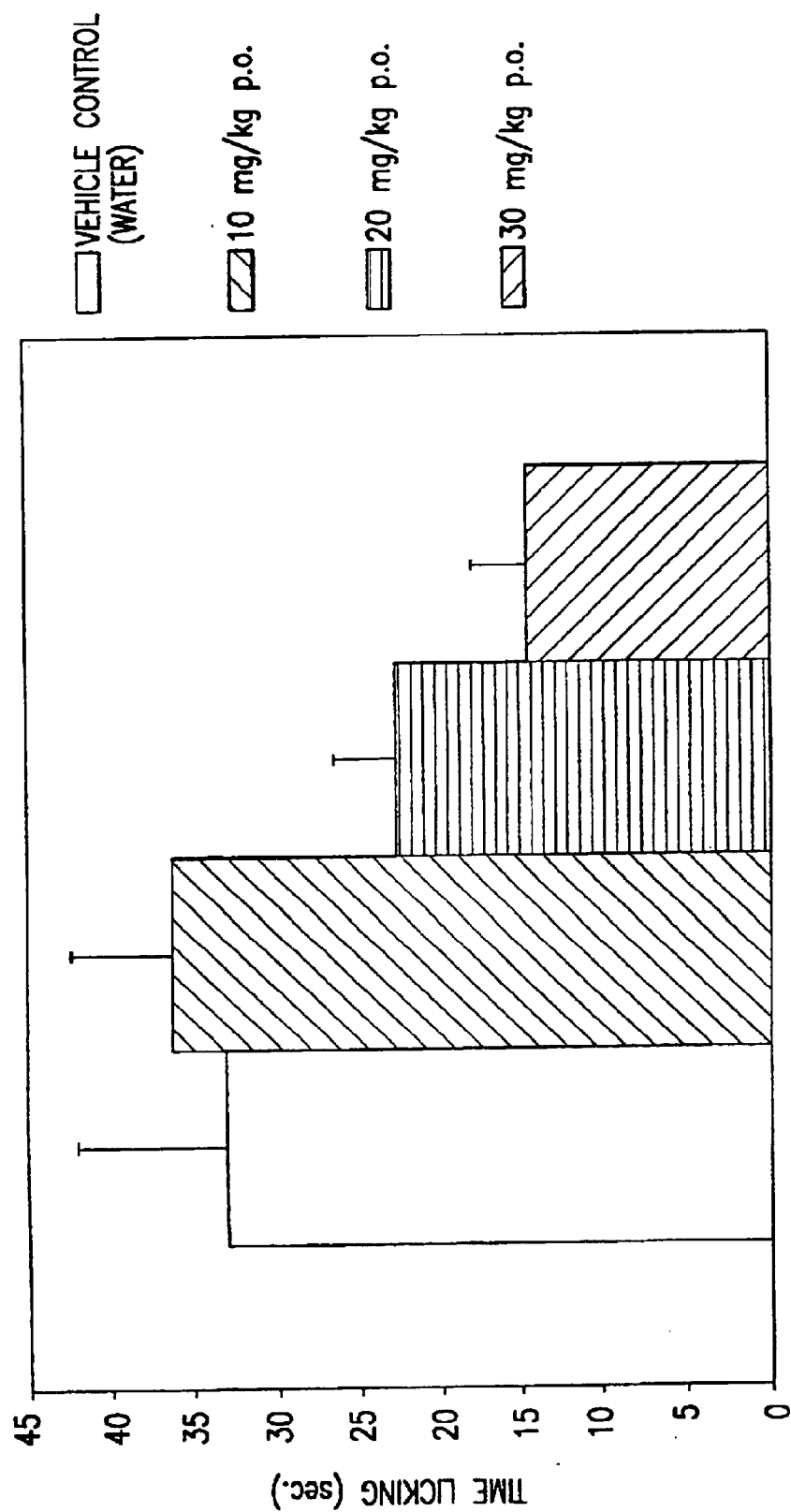
FIG. 7 is a bar graph showing the effect of 10 mg/kg (///), 20 mg/kg (≡) and 30 mg/kg (///) orally administered 1,2-di-[(N,N'-di-p-tolyl)guanidinyl]ethane, compared to vehicle control, on late phase pain in the mouse formalin test. The differences between means significant at P<0.05 by ANOVA. 30 mg/kg vs control vehicle significant at P<0.05 by post-hoc Newman-Kuels test.
Figure 8:
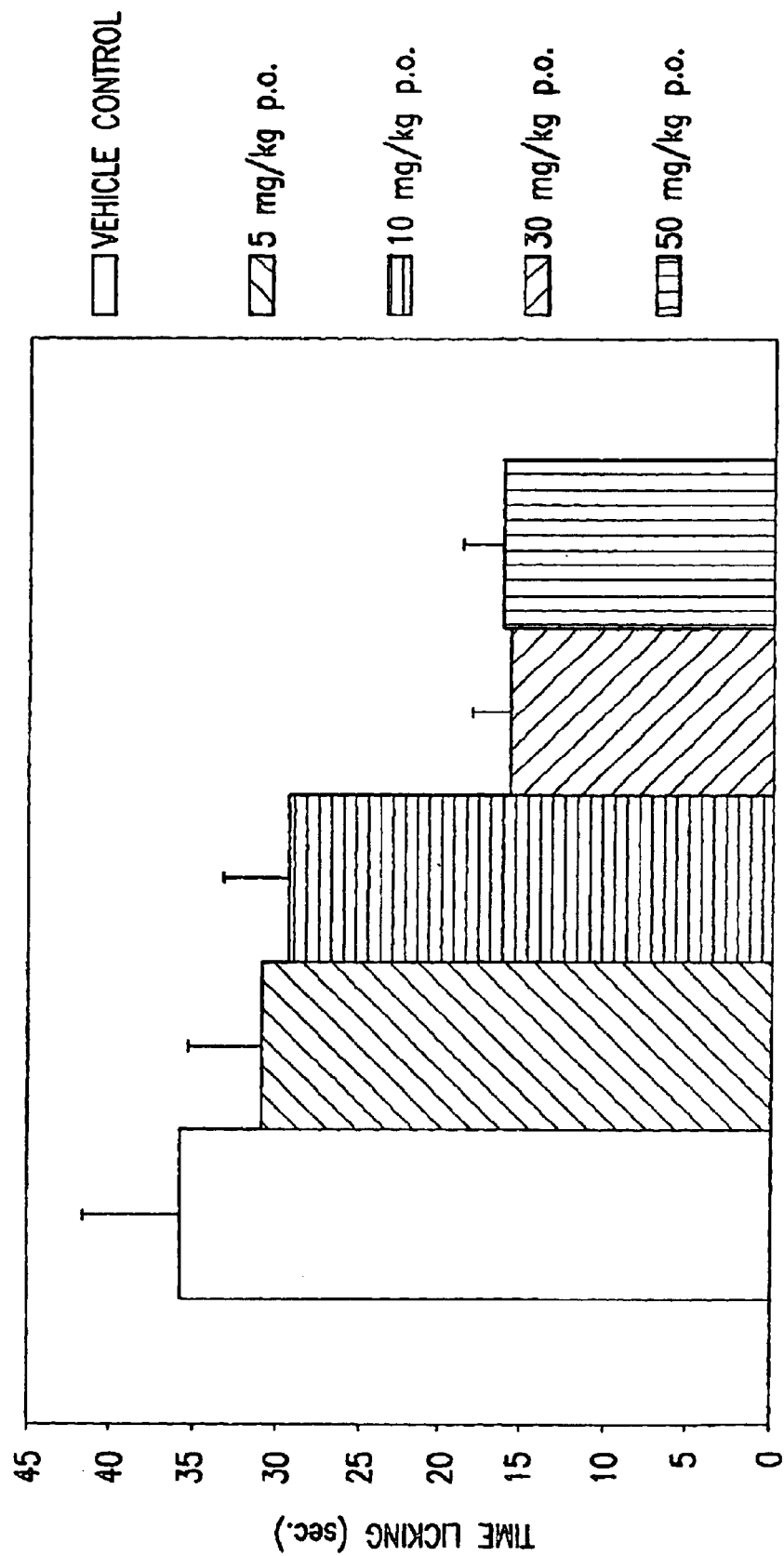
FIG. 8 is a bar graph showing the effect of 5 mg/kg (///), 10 mg/kg (≡), 30 mg/kg (///) and 50 mg/kg (∥) orally administered 1-[(N,N'-di-p-tolyl)guanyl]-4(trans 1'-cinammyl)piperizine, compared to vehicle control, on late phase pain in the mouse formalin test. Significant differences between means at P<0.01 by ANOVA. 30 and 50 mg/kg different from control vehicle at P<0.05 by post-hoc Newman-Kuels test.

The results are depicted in FIGS. 7 and 8. Both 1-[(N, N'-di-p-tolyl)guanyl]-4(trans-1'-cinnamyl)piperizine and 1,2di-[(N,N'-di-tolyl)guanidinyl]ethane produced dose-dependent reduction in the time spent licking following oral administration in the mouse formalin model of pain. This effect was observed at doses that did not affect the general behavior of the animals tested. These observations support the utility of these compounds for the treatment of chronic pain.

Having now fully described this invention, it will be understood to those of ordinary skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

What is claimed is:

1. A compound of formula I:

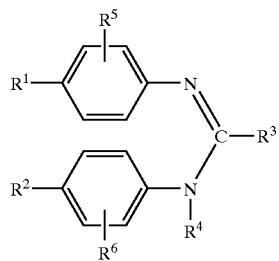

(I)

wherein, $R^1$ and $R^2$ are each independently selected from the group consisting of (a) hydrogen, halogen, hydroxy, cyano, amino, nitro, acylamido, thiol, azido, formyl, carboxy, carbonylamido and (b) aryl, fused aryl, carbocyclic, heterocyclic, heteroatyl, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, acyloxy, alkoxy, alkylthiol, alkoxyalkyl and alkylthioalkyl, each of which is optionally substituted by one or more substituents independently selected from the group consisting of halogen, hydroxy, cyano, methoxy, amino, nitro, acylamido, thiol, azido, formyl, carboxy and carbonylamido;

$R^3$ is

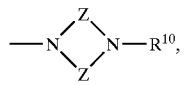

$R^4$ is selected from the group consisting of (a) hydrogen said (b) aryl, fused aryl, carbocyclic, heterocyclic, heteroaryl, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, alkoxyalkyl and akylthioalkyl, COR, $CO_2R$ and $CONR_xR_y$, each of which is optionally substituted by one or more substituents selected from the group consisting of halogen, hydroxy, cyano, methoxy, amino, nitro, acylamido, thiol, azido, formyl, carboxy and carbonylamido, wherein R, $R_x$ and $R_y$, are independently selected from the group consisting of hydrogen, aryl, fused aryl, carbocyclic, heterocyclic, heteroaryl, alkyl alkenyl, alkynyl, alkoxyalkyl, alkylthioalkyl, arylalkyl, arylalkenyl, arylalkynyl, heteroarylalkyl, heteroarylalkenyl, heteroalkynyl, carbocycloalkyl and heterocycloalkyl; or $R_x$ and $R_y$ are taken together to form a heterocycle, which is optionally substituted by one or more substituents independently selected from the group consisting of halogen, hydroxy, cyano, methoxy, amino, nitro, acylamido, thiol, azido, formyl, carboxy and carbonylamido;

$R^5$ and $R^6$ are each zero to four substituents and are independently selected from the group consisting of (a) halogen, hydroxy, cyano, amino, nitro, acylamido, thiol, azido, formyl, carboxy, carbonylamido and (b) aryl, fused aryl, carbocyclic, heterocyclic, heteroaryl, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, acyloxy, alkoxy, alkylthiol, alkoxyalkyl and alkylthioalkyl, each of which is optionally substituted by one or more substituents independently selected from the group consisting of halogen, hydroxy, cyano, methoxy, amino, nitro, acylamido, thiol, azido, formyl, carboxy and carbonylamido;

$R^7$ is selected from the group consisting of (a) hydrogen and (b) aryl fused aryl, carbocyclic, heterocyclic, heteroaryl, alkyl, alkenyl, alkynyl, alkoxyalkyl, alkylthioalkyl, arylalkyl, arylalkenyl, arylalkynyl, heteroarylalkyl, heteroarylalkenyl, heteroarylalkynyl, carbocycloalkyl, heterocycloalkyl, COR, $CO_2R$ and $CONR_XR_Y$, each of which is optionally substituted by one or more substituents independently selected from the group consisting of halogen, hydroxy, cyano, methoxy, amino, nitro, acylamido, thiol, azido, formyl, carboxy and carbonylamido, wherein R, $R_x$ and $R_y$, are independently selected from the group consisting of hydrogen, aryl, fused aryl, carbocyclic, heterocyclic, heteroaryl, alkyl, alkenyl, alkynyl, alkoxyalkyl, alkylthioalkyl, arylalkyl, arylalkenyl, arylalkynyl, heteroarylalkyl, heteroarylalkenyl, heteroalkynyl, carbocycloalkyl and heterocycloalkyl; or R, and $R_Y$ are taken together to form a heterocycle, which is optionally substituted by one or more substituents independently selected from the group consisting of halogen, hydroxy, cyano, methoxy, amino, nitro, acylamido, thiol, azido, formyl, carboxy and carbonylamido;

where $R^1$, $R^2$, $R^4$, $R^5$, $R^6$ and $R^7$ are defined above; and $R^{10}$ is selected from the group consisting of (a) hydrogen and (b) aryl, fused aryl, carbocyclic, heterocyclic, heteroaryl, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, alkoxyalkyl, alkylthioalkyl, COR, $CO_2R$ and $CONR_xR_y$, each of which is optionally substituted by one or more substituents independently selected from the group consisting of halogen, hydroxy, cyano, methoxy, amino, nitro, acylamido, thiol, azido, formyl, carboxy and carbonylamido, wherein R, $R_x$ and $R_y$ are independently selected from the group consisting of hydrogen, aryl, fused aryl, carbocyclic, heterocyclic, heteroaryl, alkyl, alkenyl, alkynyl, alkoxyalkyl, alkylthioalkyl, arylalkyl, arylalkenyl, arylalkynyl, heteroarylalkyl, heteroarylalkenyl, heteroalkynyl, carbocycloalkyl and heterocycloalkyl; or $R_x$ and $R_y$ are taken together to form a heterocycle, which is optionally substituted by one or more substituents independently selected from the group consisting of halogen, hydroxy, cyano, methoxy, amino, nitro, acylamido, thiol, azido, formyl, carboxy and carbonylamido; or $R^{10}$ is

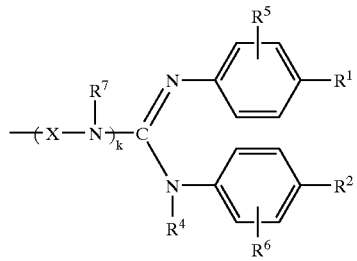

where $R^1$, $R^2$, $R^4$, $R^5$, $R^6$ and $R^7$ are defined above; k is 0 or 1 and X is a $(C_{1-6})$alkylene group, which is optionally substituted by one or more substituents independently selected from the group consisting of (a) halogen, hydroxy, cyano, amino, nitro, acylamido, thiol, azido, formyl, carboxy, carbonylamido and (b) aryl, fused aryl, carbocyclic, heterocyclic, heteroaryl, alkyl, alkenyl, alkynyl, arylalkyl, arylalkenyl, arylalkynyl, heteroarylalkyl, heteroarylalkenyl, heteroarylalkynyl, carbocycloalkyl heterocycloalkyl, acyloxy, alkoxy, alklythiol, alkoxyalkyl and alkylthioalkyl, each of which is optionally substituted by one or more substituents independently selected from the group consisting of halogen, hydroxy, cyano, methoxy, amino, nitro, acylamido, thiol, azido, formyl, carboxy and carbonylamido;

with the proviso that (a) when $R^1$ and $R^2$ are both methyl, $R^3$ is not cyclohexylamino, (b) when $R^1$, $R^2$, $R^5$ and $R^6$ comprise not more than three substitutents other than hydrogen, $R^3$ is not $(C_{1-6})$alkylamino, di$(C_{1-6})$alkylamino, unsubstituted piperazinyl or N—$(C_{1-6})$alkylpiperazinyl and (c) when Y is ethylene, at least one of the group consisting of $R^1$, $R^2$, $R^4$, $R^5$, $R^6$ and $R^7$ is other than hydrogen; or the pharmaceutically acceptable salts or esters thereof.

2. The compound of claim 1, wherein $R^{10}$ is hydrogen or optionally substituted alkyl.

3. The compound of claim 1, wherein $R^{10}$ is optionally substituted alkenyl.

4. The compound of claim 1, wherein $R^{10}$ is

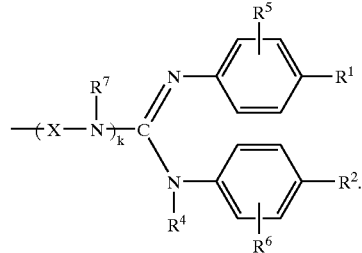

5. A pharmaceutical composition comprising the compound of claim 1 and a pharmaceutically acceptable carrier.

6. The pharmaceutical composition of claim 5, wherein the compound is 1-[(N,N'-di-p-tolyl)amidino]-4-(trans-1'-cinnamyl)piperizine.

* * * * *